US012472082B2

(12) United States Patent
Ichimura et al.

(10) Patent No.: US 12,472,082 B2
(45) Date of Patent: Nov. 18, 2025

(54) MEDICAL TUBULAR BODY DELIVERY DEVICE AND METHOD FOR MANUFACTURING THE SAME

(71) Applicant: KANEKA CORPORATION, Osaka (JP)

(72) Inventors: Shizuo Ichimura, Settsu (JP); Kentaro Suzuki, Settsu (JP); Mei Kojima, Settsu (JP)

(73) Assignee: KANEKA CORPORATION, Osaka (JP)

( * ) Notice: Subject to any disclaimer, the term of this patent is extended or adjusted under 35 U.S.C. 154(b) by 959 days.

(21) Appl. No.: 17/442,034

(22) PCT Filed: Mar. 6, 2020

(86) PCT No.: PCT/JP2020/009764
§ 371 (c)(1),
(2) Date: Sep. 22, 2021

(87) PCT Pub. No.: WO2020/195720
PCT Pub. Date: Oct. 1, 2020

(65) Prior Publication Data

US 2022/0175564 A1 Jun. 9, 2022

(30) Foreign Application Priority Data

Mar. 25, 2019 (JP) ................................ 2019-057272

(51) Int. Cl.
*A61F 2/966* (2013.01)
*A61M 25/01* (2006.01)
*A61M 25/09* (2006.01)

(52) U.S. Cl.
CPC ......... *A61F 2/966* (2013.01); *A61M 25/0147* (2013.01); *A61M 25/09* (2013.01)

(58) Field of Classification Search
CPC ....................... A61F 2002/9511; A61F 2/966; A61F 2/2466; A61F 2/95; A61M 25/09025;
(Continued)

(56) References Cited

U.S. PATENT DOCUMENTS 8,075,606 B2 12/2011 Dorn
2006/0259124 A1 11/2006 Matsuoka et al.
(Continued)

FOREIGN PATENT DOCUMENTS

JP 2006-271565 A 10/2006
JP 2008-86465 A 4/2008
(Continued)

OTHER PUBLICATIONS

Loschak, Paul. A four degree of freedom robot for positioning ultrasound imaging catheters. Journal of Mechanisms and Robotics. vol. 8, Issue 5. (Year: 2016).*
(Continued)

*Primary Examiner* — Christie Bahena
(74) *Attorney, Agent, or Firm* — Birch, Stewart, Kolasch & Birch, LLP

(57) ABSTRACT

Provided are a medical tubular body delivery device that allows frictional resistance between an outer tube and another member to be reduced and manipulation resistance during pulling of the outer tube to be reduced, thereby making it easy to handle the outer tube, and that allows indwelling of a medical tubular body to be stably performed; and a method for manufacturing the same. A device for delivering a medical tubular body into a body, the device comprising: an outer tube having a lumen in which the medical tubular body is disposed; a traction member connected to the outer tube; a traction member housing tube having a lumen into which the traction member is inserted; a guide wire tube having a lumen into which a guide wire is to be inserted; a covering tube having a lumen in which the traction member housing tube and the guide wire tube are
(Continued)

disposed; and a protective tube having a lumen in which the covering tube is disposed, wherein the traction member housing tube and the guide wire tube are fixed to each other on a distal side with respect to a distal end of the covering tube and on a proximal side with respect to a proximal end of the outer tube, and the traction member housing tube and the guide wire tube are not fixed to each other at a portion where the covering tube exists.

10 Claims, 5 Drawing Sheets

(58) Field of Classification Search
CPC .......... A61M 25/0013; A61M 25/0138; A61M 25/09; A61M 25/0021; A61M 2025/0037; B25J 9/0006; A61B 2017/00318; A61B 2017/003
See application file for complete search history.

(56) References Cited

U.S. PATENT DOCUMENTS

2008/0004606 A1* 1/2008 Swain ............. A61M 25/09025 606/1
2010/0076541 A1 3/2010 Kumoyama
2010/0331953 A1 12/2010 Matsuoka et al.

FOREIGN PATENT DOCUMENTS

JP 2008-272262 A 11/2008
JP 2008272374 A * 11/2008
JP 2013-248332 A 12/2013
JP 2017-42236 A 3/2017

OTHER PUBLICATIONS

Swain. Translation of JP2008272374A (Year: 2007).*
International Search Report for PCT/JP2020/009763 mailed on May 26, 2020.
International Search Report for PCT/JP2020/009764 mailed on May 26, 2020.
Written Opinion of the International Searching Authority for International Application No. PCT/JP2020/009763, dated May 26, 2020, with an English translation.
Written Opinion of the International Searching Authority for International Application No. PCT/JP2020/009764, dated May 26, 2020, with an English translation.

* cited by examiner

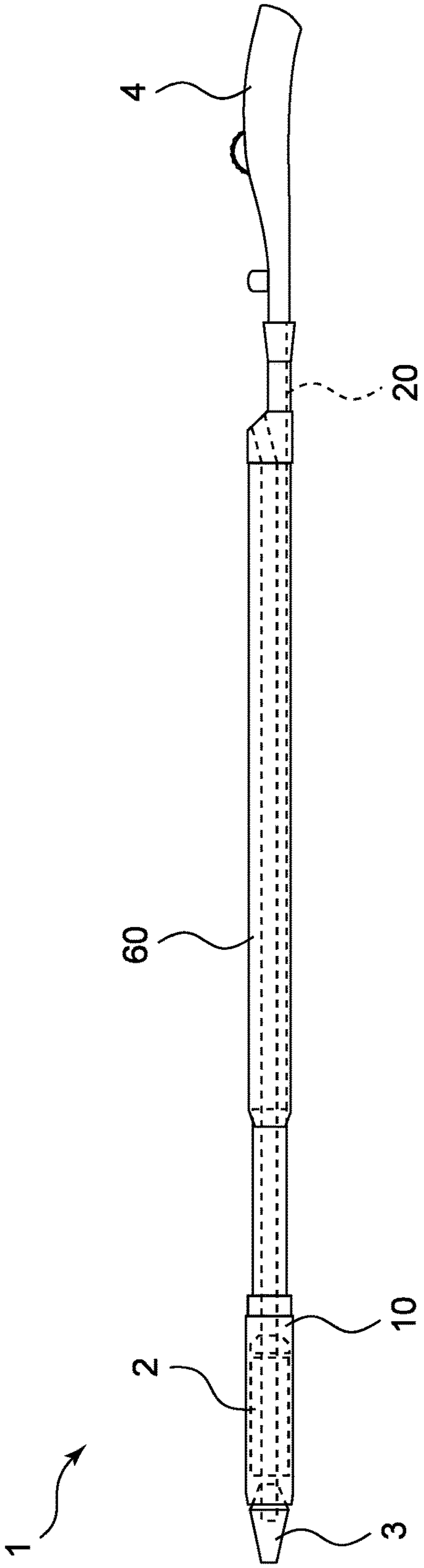
【Fig. 1】

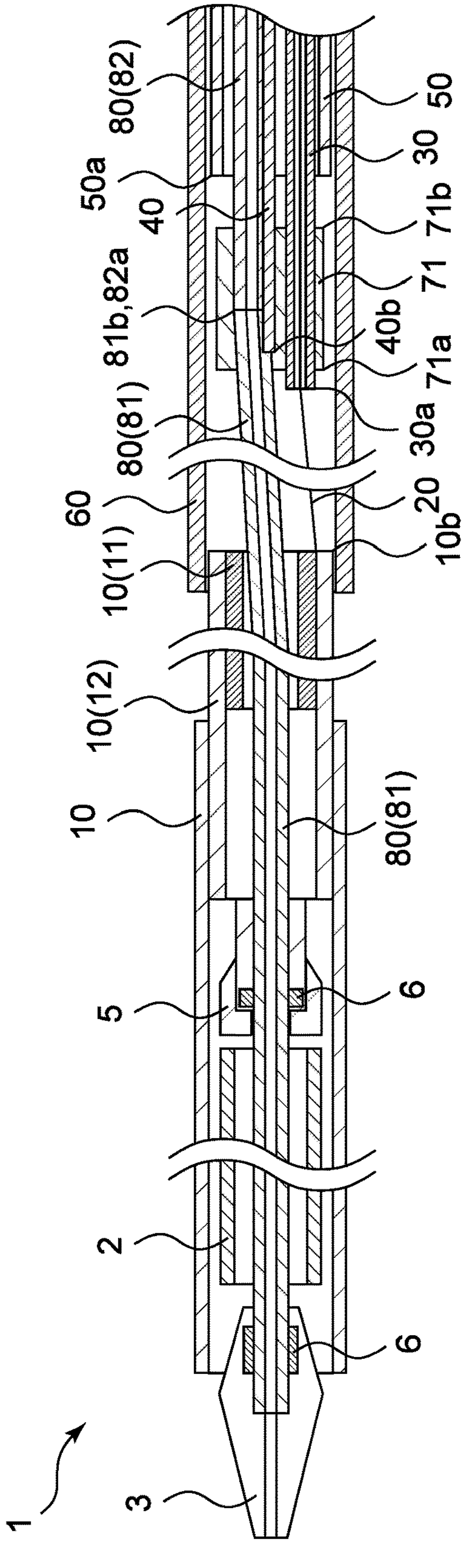
【Fig. 2】

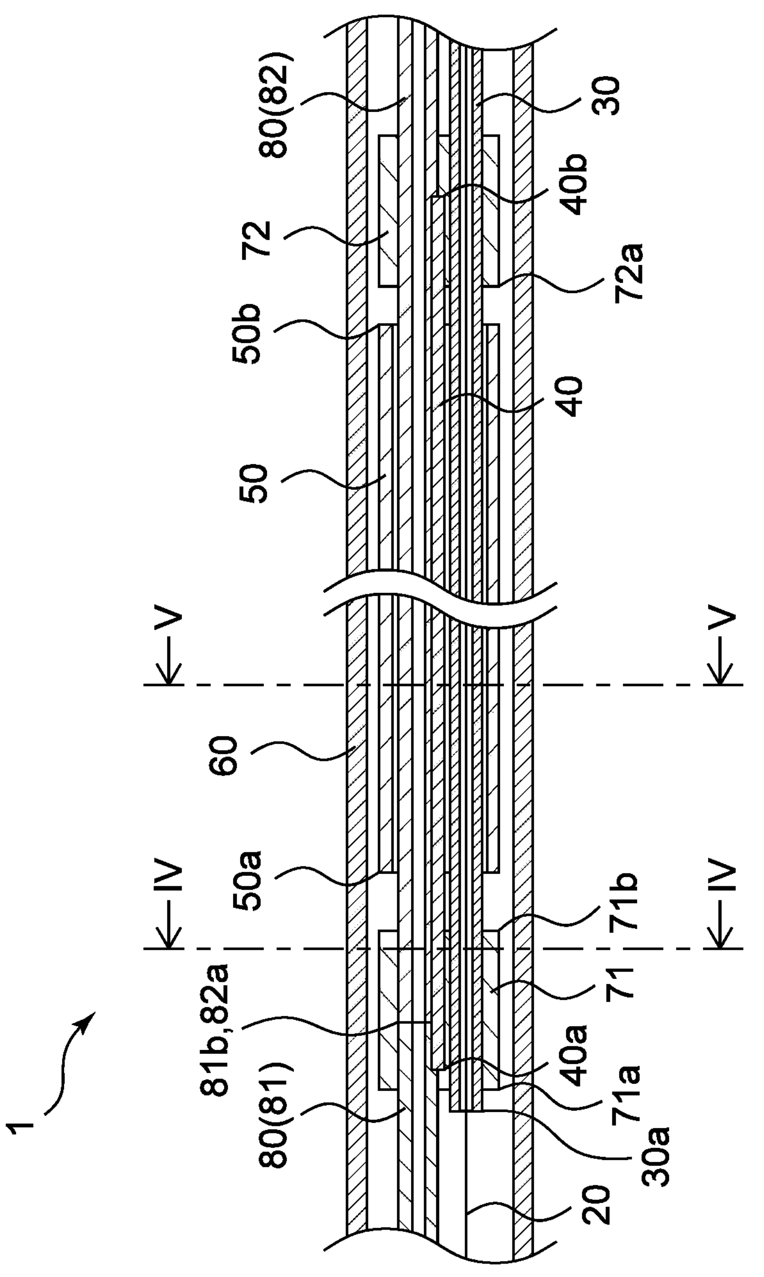
【Fig. 3】

【Fig. 4】
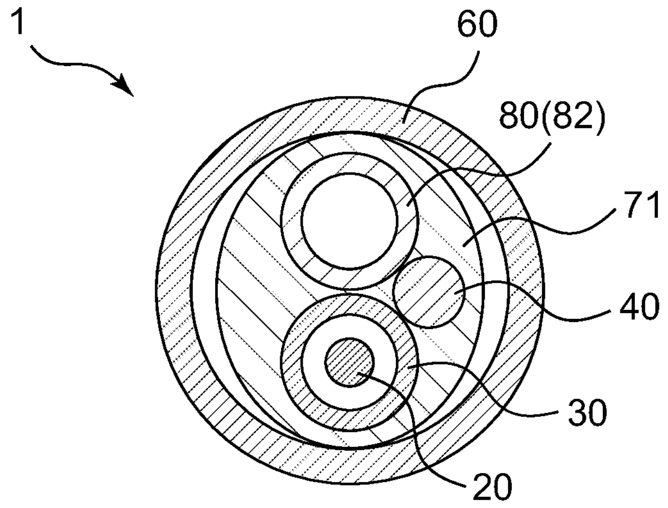

【Fig. 5】
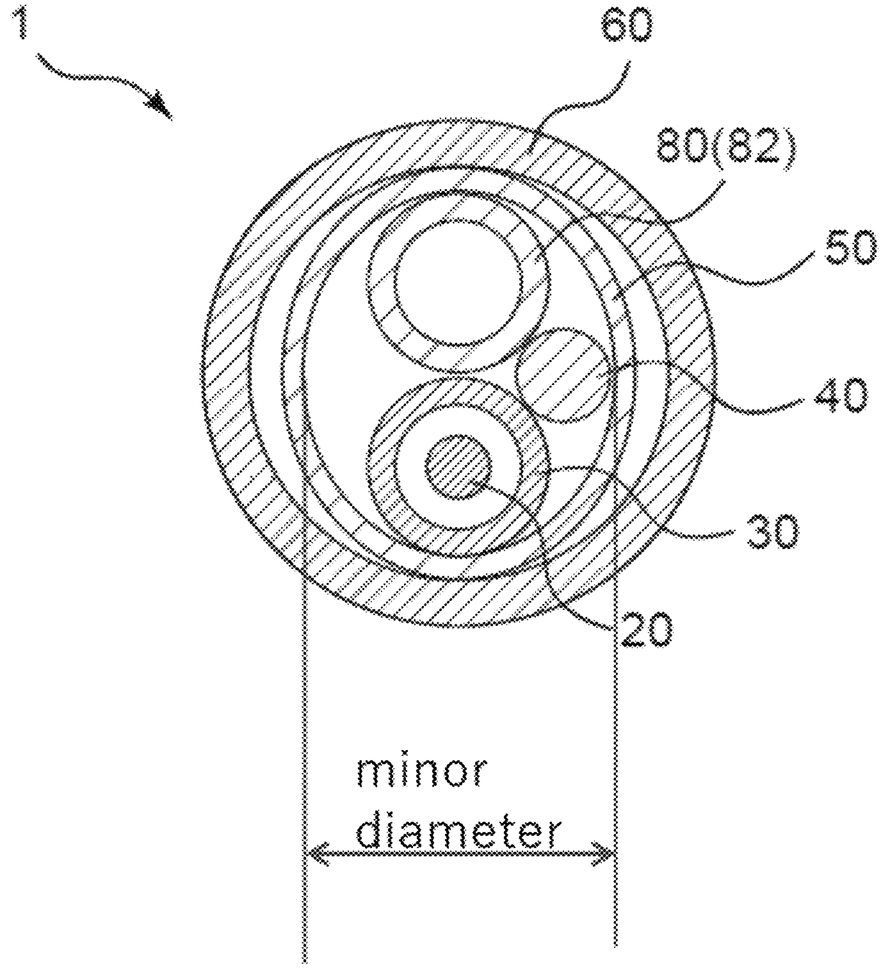

MEDICAL TUBULAR BODY DELIVERY DEVICE AND METHOD FOR MANUFACTURING THE SAME

TECHNICAL FIELD

The present invention relates to a medical tubular body delivery device which is a device for delivering a medical tubular body into a body, and a method for manufacturing the same.

BACKGROUND ART

A medical tubular body represented by a stent is a medical instrument for treating various diseases caused by stenosis or occlusion of in-vivo lumens including gastrointestinal tracts such as bile ducts and pancreatic ducts, blood vessels such as iliac arteries, etc. Examples of the medical tubular body include a tubular body that expands a lesion site such as a stenosis or occlusion site from the inside and indwells in the lesion site in order to maintain the inner diameter of the lumen, and a tubular body that entangles a thrombus or the like generated at or around a lesion site and removes the thrombus or the like from the body to restore the inner diameter of the lumen at the lesion site.

As an example of treatment with a medical tubular body using an endoscope, a method for causing a medical tubular body to dwell in a biliary tract occluded by bile duct cancer in order to cause discharge (drainage) of bile from a bile duct to the duodenal side will be described below. First, an endoscope is inserted from the mouth to the entrance (papilla) of the bile duct of the duodenum. Next, a guide wire is delivered to the lesion site through the endoscope. Furthermore, a medical tubular body delivery device is delivered to the lesion site along the guide wire. Then, the medical tubular body delivery device is manipulated to cause the medical tubular body to indwell at the lesion site.

Medical tubular body delivery devices include: a stent delivery system having a pulling manipulation portion for moving an outer tube at a tube distal end relative to an inner tube, and a manipulation wire, provided to the pulling manipulation portion, for transmitting a pulling force to the outer tube (see, for example, Patent Document 1); a stent delivery system in which a ring inside a catheter is interposed between the inner surface of a stent and the outer surface of an inner tube, and the outer surface of the ring is brought into close contact with the inner surface of the stent, in order to prevent a jumping phenomenon that the stent jumps over a treatment site and is caused to indwell at an unintended location (see, for example, Patent Document 2); a living organ expansion instrument which includes a pulling wire for moving a stent-housing tubular member to a proximal end side and in which a distal end of the wire is fixed to the inner surface of the stent-housing tubular member and movement of an outer tube for releasing a stent is easy (see, for example, Patent Document 3); a living organ expansion instrument which has a pulling wire for pulling a stent-housing tubular member and has a distal-end-side tube near a stent and in which the pulling wire is less likely to be twisted (see, for example, Patent Document 4); and a living organ expansion instrument in which the outer diameter of a proximal-end-side tube is smaller than the outer diameter of a maximum-diameter portion on the distal end side with respect to the proximal-end-side tube and which allows work for replacement with another living organ expansion instrument to be easily performed during stent indwelling work (see, for example, Patent Document 5).

PRIOR ART DOCUMENTS

Patent Documents

Patent Document 1: JP 2017-42236 A
Patent Document 2: JP 2013-248332 A
Patent Document 3: JP 2008-86465 A
Patent Document 4: JP 2008-272262 A
Patent Document 5: JP 2006-271565 A

SUMMARY OF INVENTION

Problems to be Solved by the Invention

In each of the medical tubular body delivery devices as described in Patent Documents 1 to 5, a medical tubular body is disposed in the lumen of an outer tube, and an inner tube is disposed in the lumen of the medical tubular body. By fixing the inner tube and pulling the outer tube toward the hand side of an operator, the medical tubular body is released from the medical tubular body delivery device. In each of the medical tubular body delivery devices as described in Patent Documents 1 to 5, when the outer tube is pulled toward the hand side of the operator, the entirety of the medical tubular body delivery device may move to the hand side of the operator until a force by which the inner tube presses the medical tubular body toward the side opposite to the hand side of the operator acts, so that the position of the medical tubular body may be shifted from the lesion site, or if the medical tubular body is a stent, the length in the distal-proximal direction of the medical tubular body may be extended.

Moreover, in each of the medical tubular body delivery devices as described in Patent Documents 1 to 5, there is also a problem that, if an attempt is made to release the medical tubular body such as a stent in a state where a shaft is bent, the inner tube moves toward the side opposite to the hand side of the operator in the middle of indwelling of the medical tubular body, and the length in the distal-proximal direction of the medical tubular body is compressed. Furthermore, since the outer tube of the medical tubular body delivery device interferes with another member such as the inner tube over the overall length in the distal-proximal direction, the frictional resistance between the outer tube and the other member is large in a state where the shaft is curved, for example, especially when the shaft is bent, so that it may be difficult to move the outer tube in the distal-proximal direction. Therefore, a medical tubular body delivery device that makes it easy to move an outer tube in the distal-proximal direction is desired.

The present invention has been made in view of the above circumstances, and an object of the present invention is to provide: a medical tubular body delivery device that allows frictional resistance between an outer tube and another member to be reduced and manipulation resistance during pulling of the outer tube to be reduced, thereby making it easy to handle the outer tube, and that allows indwelling of a medical tubular body to be stably performed; and a method for manufacturing the same.

Solutions to the Problems

A medical tubular body delivery device of the present invention that has solved the above problems comprising: a medical tubular body delivery device for delivering a medical tubular body into a body; an outer tube having a lumen in which the medical tubular body is disposed; a traction member connected to the outer tube; a traction member housing tube having a lumen into which the traction member is inserted; a guide wire tube having a lumen into which a guide wire is to be inserted; a covering tube having a lumen in which the traction member housing tube and the guide wire tube are disposed; and a protective tube having a lumen in which the covering tube is disposed, wherein the traction member housing tube and the guide wire tube are fixed to each other on a distal side with respect to a distal end of the covering tube and on a proximal side with respect to a proximal end of the outer tube, and the traction member housing tube and the guide wire tube are not fixed to each other at a portion where the covering tube exists.

The medical tubular body delivery device is preferable wherein, in a cross-section orthogonal to an axial direction of the covering tube, a minor diameter of the lumen of the covering tube is smaller than a sum of an outer diameter of the traction member housing tube and an outer diameter of the guide wire tube.

The medical tubular body delivery device is preferable wherein the traction member housing tube and the guide wire tube are fixed to each other on the proximal side with respect to a proximal end of the covering tube.

The medical tubular body delivery device is preferable wherein a thickness of the covering tube is smaller than a thickness of the protective tube, a thickness of the outer tube, and a thickness of the guide wire tube.

The medical tubular body delivery device is preferable wherein the guide wire tube has a distal-side guide wire tube and a proximal-side guide wire tube, a proximal end of the distal-side guide wire tube is located on the proximal side with respect to a distal end of a distal-side fixing portion at which the traction member housing tube and the guide wire tube are fixed to each other on the distal side with respect to the distal end of the covering tube and on the proximal side with respect to the proximal end of the outer tube, and a distal end of the proximal-side guide wire tube is located on the distal side with respect to a proximal end of the distal-side fixing portion.

The medical tubular body delivery device is preferable further comprising a wire disposed outward of the traction member housing tube, wherein the traction member housing tube, the guide wire tube, and the wire are fixed to each other on the distal side with respect to the distal end of the covering tube.

The medical tubular body delivery device is preferable wherein, in the cross-section orthogonal to the axial direction of the covering tube, the minor diameter of the lumen of the covering tube is smaller than a sum of outer diameters of two members having larger outer diameters out of the traction member housing tube, the guide wire tube, and the wire.

The medical tubular body delivery device is preferable wherein a distal end of the wire is located on the proximal side with respect to the distal end of the distal-side fixing portion and on the distal side with respect to the proximal end of the distal-side fixing portion at which the traction member housing tube and the guide wire tube are fixed to each other on the distal side with respect to the distal end of the covering tube and on the proximal side with respect to the proximal end of the outer tube.

The medical tubular body delivery device is preferable wherein a proximal end of the wire is located on the distal side with respect to the proximal end of the covering tube.

A method for manufacturing a medical tubular body delivery device of the present invention that has solved the above problems comprising: a first step of inserting the traction member housing tube into the lumen of the covering tube; a second step of inserting the guide wire tube into the lumen of the covering tube; and a third step of fixing the traction member housing tube and the guide wire tube to each other on the distal side with respect to the distal end of the covering tube.

The method for manufacturing a medical tubular body delivery device is preferable wherein in the first step, a proximal end of the traction member housing tube is inserted into the lumen of the covering tube through the distal end of the covering tube, and in the second step, the proximal end of the guide wire tube is inserted into the lumen of the covering tube through the distal end of the covering tube.

Effects of the Invention

With the medical tubular body delivery device of the present invention, large frictional resistance is less likely to be generated between the outer tube and another member when moving the outer tube in the distal-proximal direction, so that the manipulation resistance of the medical tubular body delivery device can be reduced. In addition, since the protective tube is included, the rigidity of the medical tubular body delivery device can be increased, it can be easy to move the outer tube in the distal-proximal direction, and indwelling of the medical tubular body can be stably performed.

BRIEF DESCRIPTION OF THE DRAWINGS

FIG. 1 shows a plan view of the entirety of a medical tubular body delivery device according to an embodiment of the present invention.

FIG. 2 shows a cross-sectional view of a distal side of the medical tubular body delivery device shown in FIG. 1, along a distal-proximal direction.

FIG. 3 shows a cross-sectional view of a proximal side of the medical tubular body delivery device shown in FIG. 1, along the distal-proximal direction.

FIG. 4 shows a IV-IV cross-sectional view of the medical tubular body delivery device shown in FIG. 3.

FIG. 5 shows a V-V cross-sectional view of the medical tubular body delivery device shown in FIG. 3.

MODE FOR CARRYING OUT THE INVENTION

Hereinafter, the present invention will be more specifically described based on the following embodiments. However, the present invention is not limited to the following embodiments and, as a matter of course, can also be carried out with appropriate modifications being made within the scope of the gist described above and below, and any of these modifications are included in the technical scope of the present invention. In any of the drawings, hatching, reference characters for members, or the like may be omitted for convenience. In this case, see the description and the other drawings. Since priority is given to facilitating the understanding of the characteristics of the present invention, the dimensions of various members in the drawings may be different from actual dimensions.

FIG. 1 is a plan view of the entirety of a medical tubular body delivery device according to an embodiment of the present invention, FIG. 2 and FIG. 3 are each a cross-sectional view of the medical tubular body delivery device along a distal-proximal direction, and FIG. 4 and FIG. 5 are each a cross-sectional view of the medical tubular body delivery device, perpendicular to the distal-proximal direction. FIG. 1 shows a configuration example of a so-called over-the-wire type medical tubular body delivery device in which a guide wire is inserted from a distal side of a shaft to a proximal side of the shaft. The present invention can also be applied to a so-called rapid exchange type medical tubular body delivery device in which a wire is inserted halfway from a distal side of a shaft to a proximal side of the shaft.

In the present invention, the proximal side refers to the hand side of the user in a direction in which an outer tube 10 or a protective tube 60 extends, and the distal side refers to the side opposite to the proximal side, that is, the treatment target side. In addition, the direction in which the outer tube 10 or the protective tube 60 extends is referred to as a distal-proximal direction. A radial direction refers to the radial direction of the outer tube 10 or the protective tube 60, a radially inward direction refers to the direction toward the axial center side of the outer tube 10 or the protective tube 60, and a radially outward direction refers to the direction toward the side opposite to the radially inner side. In FIG. 1 to FIG. 3, the right side of the drawing is the proximal side, and the left side of the drawing is the distal side.

The medical tubular body delivery device 1 of the present invention is a device that delivers a medical tubular body 2 into a body. Examples of the medical tubular body 2 include a stent, a stent graft, an occlusion tool, an injection catheter, and a prosthesis valve. Among them, the stent is generally used for treating various diseases caused by stenosis or occlusion of in-vivo lumens including gastrointestinal tracts such as bile ducts, blood vessels, etc. Examples of the stent include a coil-shaped stent formed from one linear metal, a stent obtained by cutting a metal tube with a laser, a stent assembled by welding a linear member with a laser, a stent made by weaving a plurality of linear metals, and stents having the same shapes as these metal stents and formed from a polymer material.

As shown in FIG. 1 to FIG. 3, the medical tubular body delivery device 1 includes the outer tube 10 having a lumen in which the medical tubular body 2 is disposed, a traction member 20 connected to the outer tube 10, a traction member housing tube 30 having a lumen into which the traction member 20 is inserted, a guide wire tube 80 having a lumen into which a guide wire is inserted, a covering tube 50 having a lumen in which the traction member housing tube 30 and the guide wire tube 80 are disposed, and the protective tube 60 having a lumen in which the covering tube 50 is disposed.

In the medical tubular body delivery device 1, the traction member housing tube 30 and the guide wire tube 80 are fixed to each other on the distal side with respect to a distal end 50*a* of the covering tube 50 and on the proximal side with respect to a proximal end 10*b* of the outer tube 10, and the traction member housing tube 30 and the guide wire tube 80 are not fixed to each other at a portion where the covering tube 50 exists. In the medical tubular body delivery device 1, since the traction member housing tube 30 and the guide wire tube 80 are fixed to each other on the distal side with respect to the distal end 50*a* of the covering tube 50 and on the proximal side with respect to the proximal end 10*b* of the outer tube 10, and the traction member housing tube 30 and the guide wire tube 80 are not fixed to each other at the portion where the covering tube 50 exists, the traction member housing tube 30 and the guide wire tube 80 are partially fixed to each other, so that a force applied to the hand side of the medical tubular body delivery device 1 is easily transmitted to the distal end, and the pushability of the medical tubular body delivery device 1 can be improved. In addition, since the traction member housing tube 30 and the guide wire tube 80 are partially not fixed to each other, the traction member housing tube 30 and the guide wire tube 80 are movable at this non-fixed portion. Therefore, in a state where the medical tubular body delivery device 1 is curved such as the case where the medical tubular body delivery device 1 is bent, each of the traction member housing tube 30 and the guide wire tube 80 can move along this curve, and the movement in the distal-proximal direction of the traction member 20 is less likely to be hindered. Thus, the movement in the distal-proximal direction of the outer tube 10 is less likely to be hindered, and indwelling of the medical tubular body 2 can be easily and stably performed. Furthermore, since the traction member housing tube 30 and the guide wire tube 80 are fixed to each other on the distal side with respect to the distal end 50*a* of the covering tube 50 and on the proximal side with respect to the proximal end 10*b* of the outer tube 10, and the traction member housing tube 30 and the guide wire tube 80 are not fixed to each other at the portion where the covering tube 50 exists, the medical tubular body delivery device 1 also has an effect that the manufacture of the medical tubular body delivery device 1 is facilitated as compared to that of a conventional medical tubular body delivery device.

In the present invention, the fact that the traction member housing tube 30 and the guide wire tube 80 are fixed to each other refers to a state where the traction member housing tube 30 and the guide wire tube 80 cannot move in the radial direction, the distal-proximal direction, and a circumferential direction by at least partially fixing the traction member housing tube 30 and the guide wire tube 80 to each other. In addition, in the present invention, the fact that the traction member housing tube 30 and the guide wire tube 80 are not fixed to each other refers to a state that is not a state where the traction member housing tube 30 and the guide wire tube 80 are fixed to each other. Specifically, this fact indicates that the traction member housing tube 30 and the guide wire tube 80 are disposed in the lumen of the covering tube 50 and a portion where the traction member housing tube 30 and the guide wire tube 80 are fixed to each other is present on the distal side, whereby the traction member housing tube 30 and the guide wire tube 80 cannot move in the radial direction and the distal-proximal direction relative to each other but are movable in the circumferential direction. The fact that the traction member housing tube 30 and the guide wire tube 80 move in the radial direction indicates that the traction member housing tube 30 and the guide wire tube 80 become separated from each other in a cross-section perpendicular to the distal-proximal direction. The fact that the traction member housing tube 30 and the guide wire tube 80 move in the distal-proximal direction indicates that the positional relationship between the traction member housing tube 30 and the guide wire tube 80 changes in the distal-proximal direction. The fact that the traction member housing tube 30 and the guide wire tube 80 move in the circumferential direction indicates that at least one of the traction member housing tube 30 and the guide wire tube 80 moves and the positional relationship therebetween changes in a cross-section perpendicular to the distal-proximal direction. As a method for fixing the traction member housing tube 30 and the guide wire tube 80 to each other, for example, the traction member housing tube 30 and the guide wire tube 80 are bonded, welded, fitted, or screwed, the traction member housing tube 30 and the guide wire tube 80 are inserted into a heat-shrinkable resin tube and the resin tube is heat-shrunk, or the traction member housing tube 30 and the guide wire tube 80 are inserted into a metal tube and the metal tube is crimped.

The outer tube 10 has a distal-proximal direction and has a lumen extending in the distal-proximal direction, and the medical tubular body 2 is disposed in the lumen. Examples of the material of the outer tube 10 include synthetic resins including: polyolefin-based resins such as polyethylene and polypropylene; polyamide-based resins such as nylon; polyester-based resins such as PET; aromatic polyether ketone-based resins such as PEEK; polyether polyamide-based resins; polyurethane-based resins; polyimide-based resins; fluorine-based resins such as PTFE, PFA, and ETFE; polyvinyl chloride-based resins; and the like. Among them, the material of the outer tube 10 is preferably a fluorine-based resin, and more preferably PTFE. When the material of the outer tube 10 is a fluorine-based resin, the outer tube 10 can have good slidability, and the slipperiness between the outer tube 10 and the medical tubular body 2 is improved, so that it is easy to cause the medical tubular body 2 to indwell.

Moreover, the outer tube 10 may have a single-layer structure or a multi-layer structure. In the case where the outer tube 10 has a multi-layer structure, the outer tube 10 can have, for example, a structure in which a metal braid made of stainless steel, carbon steel, a nickel-titanium alloy, or the like is used as an intermediate layer of a resin tube that forms the outer tube 10. In addition, the outer tube 10 may have a two-layer structure in which a fluorine-based resin is used for the inner layer and a polyamide-based resin is used for the outer layer.

As for the length in the distal-proximal direction of the outer tube 10, an appropriate length can be selected in accordance with the length in the distal-proximal direction of the medical tubular body 2 disposed in the lumen thereof. For example, the length in the distal-proximal direction of the outer tube 10 can be not shorter than 50 mm and not longer than 800 mm.

The outer diameter of the outer tube 10 is preferably not smaller than 0.5 mm, more preferably not smaller than 0.7 mm, and further preferably not smaller than 1 mm. When the lower limit of the outer diameter of the outer tube 10 is set to be in the above range, the rigidity of the distal side of the medical tubular body delivery device 1 on which the outer tube 10 is disposed can be increased, so that the medical tubular body delivery device 1 can have good pushability. In addition, the outer diameter of the outer tube 10 is preferably not larger than 3.5 mm, more preferably not larger than 3.3 mm, and further preferably not larger than 3.0 mm. When the upper limit of the outer diameter of the outer tube 10 is set to be in the above range, the outer diameter of the distal side of the medical tubular body delivery device 1 can be prevented from being excessively large, so that the minimal invasiveness of the medical tubular body delivery device 1 can be improved. Furthermore, it is possible to prevent the rigidity of the distal side of the medical tubular body delivery device 1 from being excessively large, and to improve the manipulability of the medical tubular body delivery device 1 at the time of delivery into a body.

The thickness of the outer tube 10 is preferably not smaller than 10 μm, more preferably not smaller than 30 μm, and further preferably not smaller than 50 μm. When the lower limit of the thickness of the outer tube 10 is set to be in the above range, the rigidity of the outer tube 10 can be increased, so that the insertability of the medical tubular body delivery device 1 can be improved. In addition, the thickness of the outer tube 10 is preferably not larger than 350 μm, more preferably not larger than 300 μm, and further preferably not larger than 250 μm. When the upper limit of the thickness of the outer tube 10 is set to be in the above range, the lumen of the outer tube 10 can be widened, so that the kinds of diameters of medical tubular bodies 2 that can be housed in the lumen of the outer tube 10 can be increased, so that it is possible to deliver various kinds of medical tubular bodies 2 by the medical tubular body delivery device 1. In the case where the outer tube 10 has a reinforcement portion 11 described later, or in the case where the outer tube 10 has the reinforcement portion 11 and a connection tube 12 described later, the thickness of the outer tube 10 at a portion where the reinforcement portion 11 and the connection tube 12 do not exist, or the thickness excluding the thicknesses of the reinforcement portion 11 and the connection tube 12, is defined as the thickness of the outer tube 10.

The traction member 20 has a distal-proximal direction and is connected to the outer tube 10. The traction member 20 is used for moving the outer tube 10 in the distal-proximal direction in order to perform indwelling of the medical tubular body 2 and the like. Specifically, for example, the traction member 20 is pulled toward the proximal side to move the outer tube 10 toward the proximal side, thereby releasing the medical tubular body 2 from the outer tube 10. In addition, in the middle of release of the medical tubular body 2 from the outer tube 10, it is also possible to adjust the indwelling location of the medical tubular body 2 by sending the traction member 20 toward the distal side to move the outer tube 10 toward the distal side such that the medical tubular body 2 is housed in the lumen of the outer tube 10 again.

The traction member 20 is preferably a linear member. The traction member 20 may be a tubular linear member having a lumen extending in the distal-proximal direction, but is more preferably a solid linear member. When the traction member 20 is a linear member, the outer tube 10 is easily moved in the distal-proximal direction. In addition, when the traction member 20 is a solid linear member, it is possible to prevent the outer diameter of the medical tubular body delivery device 1 from being excessively large.

Examples of the material of the traction member 20 include metals such as stainless steel, iron, nickel, titanium, and alloys thereof, and synthetic resins including: polyamide-based resins such as nylon; polyolefin-based resins such as PP and PE; polyester-based resins such as PET; aromatic polyether ketone-based resins such as PEEK; polyimide-based resins; fluorine-based resins such as PTFE, PFA, and ETFE; and the like, and materials obtained by combining these materials. Among them, the material of the traction member 20 is preferably stainless steel. When the material of the traction member 20 is stainless steel, the strength of the traction member 20 can be increased, so that the traction member 20 can be prevented from being broken even when the traction member 20 is repeatedly moved in the distal-proximal direction.

The traction member 20 is preferably connected to a proximal end portion of the outer tube 10. When the traction member 20 is connected to the proximal end portion of the outer tube 10, it is not necessary to dispose the outer tube 10 over the entirety in the distal-proximal direction of the medical tubular body delivery device 1, and the traction member 20 having a smaller outer diameter than the outer tube 10 can be disposed on the proximal side of the medical tubular body delivery device 1. Therefore, the outer diameter of the proximal side of the medical tubular body delivery device 1 can be decreased.

As a method for connecting the traction member 20 to the outer tube 10, for example, the traction member 20 and the outer tube 10 are bonded by an adhesive or fused by heating, the traction member 20 and the outer tube 10 are fixed by inserting the traction member 20 and the outer tube 10 into a heat-shrinkable resin tube and heat-shrinking the resin tube, or are fixed by covering the traction member 20 and the outer tube 10 with a tubular member and crimping the tubular member, the linear traction member 20 is fixed to the outer tube 10 by winding the linear traction member 20 on the outer tube 10, or the traction member 20 is fixed to the outer tube 10 by welding the end of the traction member 20 to the outer tube 10. Among them, the traction member 20 is preferably connected to the outer tube 10 by covering the traction member 20 and the outer tube 10 with a heat-shrinkable tube and heat-shrinking the tube, for example, to bring the traction member 20 and the outer tube 10 into pressure contact with the tube. When the traction member 20 is connected to the outer tube 10 by covering the traction member 20 and the outer tube 10 with a heat-shrinkable tube and heat-shrinking the tube, for example, to bring the traction member 20 and the outer tube 10 into pressure contact with each other, the traction member 20 can be easily and firmly connected to the outer tube 10.

As shown in FIG. 2, the outer tube 10 may have the reinforcement portion 11 having higher rigidity than the other portion of the outer tube 10, on the proximal side, and the traction member 20 may be connected to the reinforcement portion 11. When the traction member 20 is connected to the reinforcement portion 11 of the outer tube 10, a force applied to the traction member 20, for example, when the traction member 20 is pulled toward the proximal side is easily transmitted to the reinforcement portion 11. As a result, the outer tube 10 can be prevented from being broken.

As a method for forming the reinforcement portion 11 on the proximal side of the outer tube 10, for example, a tubular member that forms the reinforcement portion 11 is disposed on the proximal side of a tubular member that forms the outer tube 10. The tubular member that forms the reinforcement portion 11 may be disposed radially outward of the tubular member that forms the outer tube 10, but is preferably disposed inward of the tubular member that forms the outer tube 10. When the tubular member that forms the reinforcement portion 11 is disposed inward of the tubular member that forms the outer tube 10, the rigidity of the reinforcement portion 11 of the outer tube 10 can be increased. Therefore, the outer tube 10 can be less likely to be broken when a load is applied to the outer tube 10, for example, when the traction member 20 is pulled toward the proximal side.

The material of the tubular member that forms the reinforcement portion 11 is preferably a material having higher rigidity than the material of the tubular member that forms the outer tube 10. Examples of such a material include polyimide-based resins and polyamide-based resins. In addition, the tubular member that forms the reinforcement portion 11 may have a multi-layer structure including a braided layer such as a metal braid. Among them, the material of the tubular member that forms the reinforcement portion 11 is preferably a polyimide-based resin. When the material of the tubular member that forms the reinforcement portion 11 is a polyimide-based resin, it is possible to impart both flexibility and rigidity to the proximal side of the outer tube 10, and it is easy to fix the traction member 20 to the proximal end portion of the outer tube 10. Furthermore, it is possible to firmly fix a tubular member that forms the traction member 20, to the tubular member that forms the outer tube 10, so that the outer tube 10 can be prevented from being broken.

In the case where the outer tube 10 has the reinforcement portion 11 on the proximal side, the outer tube 10 may have the connection tube 12 between the tubular member that forms the outer tube 10 and the tubular member that forms the reinforcement portion 11. That is, the connection tube 12 may be disposed in the lumen of the proximal side of the tubular member that forms the outer tube 10, and the tubular member that forms the reinforcement portion 11 may be disposed in the lumen of the connection tube 12, or the connection tube 12 may be disposed outward of the proximal side of the tubular member that forms the outer tube 10, and the tubular member that forms the reinforcement portion 11 may be disposed outward of the connection tube 12. When the connection tube 12 is provided between the tubular member that forms the outer tube 10 and the tubular member that forms the reinforcement portion 11, in the case where the material of the tubular member that forms the outer tube 10 and the material of the tubular member that forms the reinforcement portion 11 are materials that are difficult to join to each other, the connection tube 12 can be used as an adhesive layer to firmly connect the tubular member that forms the outer tube 10 and the tubular member that forms the reinforcement portion 11 via the connection tube 12.

The traction member housing tube 30 has a distal-proximal direction and has a lumen extending in the distal-proximal direction, and the traction member 20 is inserted into the lumen. Since the traction member 20 is inserted into the lumen of the traction member housing tube 30, a situation in which the traction member 20 comes into contact with another member to apply stress to the traction member 20 or break the traction member 20 or the other member is prevented, so that the traction member 20 is easily moved in the distal-proximal direction. In addition, since the traction member 20 is housed in the tube cavity of the traction member housing tube 30, the traction member 20 is prevented from straying inside the medical tubular body delivery device 1, being wound on another member, or being excessively bent.

Examples of the material of the traction member housing tube 30 include metals such as stainless steel, iron, nickel, titanium, and alloys thereof, and synthetic resins including: polyolefin-based resins such as polyethylene and polypropylene; polyamide-based resins such as nylon; polyester-based resins such as PET; aromatic polyether ketone-based resins such as PEEK; polyether polyamide-based resins; polyurethane-based resins; polyimide-based resins; fluorine-based resins such as PTFE, PFA, and ETFE; polyvinyl chloride-based resins; and the like. The material of the traction member housing tube 30 is preferably a metal, and more preferably stainless steel. When the traction member housing tube 30 is formed as described above, the durability of the traction member housing tube 30 can be improved, so that the traction member housing tube 30 can be less likely to be broken even when the traction member 20 is repeatedly moved in the distal-proximal direction in a state where the traction member 20 is inserted into the lumen of the traction member housing tube 30. In addition, when stainless steel is used for the traction member housing tube 30, even if the traction member housing tube 30 has a small diameter, the traction member housing tube 30 has high rigidity, so that it is also possible to decrease the diameter of the entire medical tubular body delivery device 1. Furthermore, when the traction member housing tube 30 is connected to the guide wire tube 80, the pushability of the medical tubular body delivery device 1 can be improved, the delivery performance to a target site such as an affected area can be improved, and the medical tubular body 2 such as a stent can be easily expanded.

The thickness of the traction member housing tube 30 is preferably not smaller than 10 μm, more preferably not smaller than 20 μm, and further preferably not smaller than 30 μm. When the lower limit of the thickness of the traction member housing tube 30 is set to be in the above range, the strength of the traction member housing tube 30 is sufficient, so that the traction member housing tube 30 can be prevented from being broken even if the traction member housing tube 30 and the traction member 20 come into contact with each other when inserting the traction member 20 into the lumen of the traction member housing tube 30. In addition, the thickness of the traction member housing tube 30 is preferably not larger than 200 μm, more preferably not larger than 150 μm, and further preferably not larger than 100 μm. When the upper limit of the thickness of the traction member housing tube 30 is set to be in the above range, a situation in which the outer diameter of the traction member housing tube 30 becomes excessively large and thus the outer diameter of the medical tubular body delivery device 1 also becomes excessively large can be prevented. In addition, occurrence of excessive rigidity due to the outer diameter of the traction member housing tube 30 being excessively large can be prevented, so that appropriate manipulation performance of the medical tubular body delivery device 1 can be ensured.

The inner diameter of the traction member housing tube 30 is preferably not smaller than 1.1 times, more preferably not smaller than 1.2 times, and further preferably not smaller than 1.3 times the outer diameter of the traction member 20. When the lower limit of the inner diameter of the traction member housing tube 30 is set to be in the above range, in a state where the traction member 20 is inserted into the lumen of the traction member housing tube 30, generation of excessive friction between the traction member 20 and the traction member housing tube 30 is prevented, so that the traction member 20 is easily moved in the distal-proximal direction. In addition, the inner diameter of the traction member housing tube 30 is preferably not larger than 3 times, more preferably not larger than 2.5 times, and further preferably not larger than 2 times the outer diameter of the traction member 20. When the upper limit of the inner diameter of the traction member housing tube 30 is set to be in the above range, it is possible to prevent a situation in which the outer diameter of the traction member housing tube 30 is increased, and as a result, the outer diameter of the medical tubular body delivery device 1 at a portion where the traction member housing tube 30 exists is also increased. In addition, bending of the traction member 20 inside the traction member housing tube 30 can be suppressed, and the traction member 20 can be efficiently pulled.

The guide wire tube 80 has a distal-proximal direction and has a lumen extending in the distal-proximal direction, and the guide wire is inserted into the lumen. When the medical tubular body delivery device 1 has the guide wire tube 80, it is easy to insert the guide wire into the medical tubular body delivery device 1, so that the medical tubular body delivery device 1 can be delivered into a body along the guide wire. In addition, when the guide wire is inserted into the medical tubular body delivery device 1, the guide wire is prevented from damaging the medical tubular body delivery device 1.

Examples of the material of the guide wire tube 80 include synthetic resins including: polyolefin-based resins such as polyethylene and polypropylene; polyamide-based resins such as nylon; polyester-based resins such as PET; aromatic polyether ketone-based resins such as PEEK; polyether polyamide-based resins; polyurethane-based resins; polyimide-based resins; fluorine-based resins such as PTFE, PFA, and ETFE; polyvinyl chloride-based resins; and the like. Among them, the material of the guide wire tube 80 is preferably a polyimide-based resin. When the material of the guide wire tube 80 is a polyimide-based resin, the slipperiness of the guide wire tube 80 is improved. Therefore, it is easy to insert the guide wire into the lumen of the guide wire tube 80 and deliver the medical tubular body delivery device 1 into the body along the guide wire. In addition, the guide wire tube 80 may have a multi-layer structure including a braided layer such as a metal braid. When the guide wire tube 80 has a multi-layer structure, the tensile strength, slipperiness to the guide wire, and the kink resistance of the guide wire tube 80 can be enhanced.

The covering tube 50 has a distal-proximal direction and has a lumen extending in the distal-proximal direction, and the traction member housing tube 30 and a guide wire tube 80 are disposed in the lumen. At the portion where the covering tube 50 exists, the traction member housing tube 30 and the guide wire tube 80 are not fixed to each other. Since the traction member housing tube 30 and the guide wire tube 80 are not fixed to each other at the portion where the covering tube 50 exists, the covering tube 50 does not fix the traction member housing tube 30 and the guide wire tube 80 to each other, but the movement in the distal-proximal direction and the radial direction of the traction member housing tube 30 and the guide wire tube 80 can be hindered, and only the movement in the circumferential direction of the traction member housing tube 30 and the guide wire tube 80 can be allowed. Since the traction member housing tube 30 and the guide wire tube 80 can move in the circumferential direction at the portion where the covering tube 50 exists, a portion where stress is concentrated when the medical tubular body delivery device 1 is bent, such as in a state where the medical tubular body delivery device 1 is bent and curved, can be eliminated, and the efficiency of load transmission from the distal end of the medical tubular body delivery device 1 to the hand side of the medical tubular body delivery device 1 can be improved.

Examples of the material of the covering tube 50 include synthetic resins including: polyolefin-based resins such as polyethylene and polypropylene; polyamide-based resins such as nylon; polyester-based resins such as PET; aromatic polyether ketone-based resins such as PEEK; polyether polyamide-based resins; polyurethane-based resins; polyimide-based resins; fluorine-based resins such as PTFE, PFA, and ETFE; polyvinyl chloride-based resins; and the like. Among them, the material of the covering tube 50 is preferably a polyolefin-based resin or a fluorine-based resin, and more preferably any of a high-density polyethylene, PTFE, and PFA. These materials have a low coefficient of friction and excellent slipperiness. When the material of the covering tube 50 is a polyolefin-based resin or a fluorine-based resin, the covering tube 50 can have sufficient rigidity, and the slipperiness of the surface of the covering tube 50 can also be improved. Therefore, it is easy to insert the traction member housing tube 30 and the guide wire tube 80 into the lumen of the covering tube 50.

The material of the covering tube 50 is preferably different from the material of the traction member housing tube 30 and the material of the guide wire tube 80. When the material of the covering tube 50 is different from the material of the traction member housing tube 30 and the material of the guide wire tube 80, it is possible to improve the slipperiness between the traction member housing tube 30 and the guide wire tube 80, and the covering tube 50. If the material of the covering tube 50 is the same as the material of the traction member housing tube 30 and the material of the guide wire tube 80, resistance due to intermolecular force may occur between the members. Thus, the material of the covering tube 50 is preferably different from the material of the traction member housing tube 30 and the material of the guide wire tube 80. In particular, in the case where the covering tube 50 is thin, the material of the covering tube 50 is preferably different from the material of the traction member housing tube 30 and the material of the guide wire tube 80.

The length in the distal-proximal direction of the covering tube 50 is preferably longer than the length in the distal-proximal direction of the outer tube 10. When the length in the distal-proximal direction of the covering tube 50 is longer than the length in the distal-proximal direction of the outer tube 10, it is easy to insert the traction member 20 into the lumen of the traction member housing tube 30, so that the outer tube 10 to which the traction member 20 is connected is easily moved in the distal-proximal direction.

The length in the distal-proximal direction of the covering tube 50 is preferably not smaller than 70%, more preferably not smaller than 80%, and further preferably not smaller than 90% of the length in the distal-proximal direction of a proximal-side guide wire tube 82. When the lower limit of the ratio of the length in the distal-proximal direction of the covering tube 50 to the length in the distal-proximal direction of the proximal-side guide wire tube 82 is set to be in the above range, it can be easy to move the traction member housing tube 30 and the proximal-side guide wire tube 82, which are disposed inside the covering tube 50, in the circumferential direction, and these members can be prevented from being broken. In addition, the upper limit of the ratio of the length in the distal-proximal direction of the covering tube 50 to the length in the distal-proximal direction of the outer tube 10 is not particularly limited, but, for example, the ratio can be not larger than 105% and not larger than 100%. In addition, the covering tube 50 may be divided into a plurality of sections in the distal-proximal direction and disposed. In the case where the covering tube 50 is divided, the interval between the adjacent sections of the covering tube 50 is preferably small with respect to the length in the distal-proximal direction of the covering tube 50. Specifically, the interval between the adjacent sections of the covering tube 50 is preferably not larger than 10% and more preferably not larger than 5% of the length in the distal-proximal direction of the covering tube 50. In the case where the covering tube 50 is divided into a plurality of sections in the distal-proximal direction and disposed, when the lower limit of the interval between the adjacent sections of the covering tube 50 is set to be in the above range, the covering tube 50 easily exhibits an effect as a non-fixed portion.

Examples of the shape of the lumen of the covering tube 50 in a cross-section, of the covering tube 50, orthogonal to the distal-proximal direction include a circular shape, an elliptical shape, a polygonal shape, and a porous shape. Among them, the shape of the lumen of the covering tube 50 is preferably an elliptical shape. When the shape of the lumen of the covering tube 50 is an elliptical shape, excessive movement of the traction member housing tube 30 and the guide wire tube 80, which are disposed in the lumen of the covering tube 50, can be prevented while bringing the traction member housing tube 30 and the guide wire tube 80 into a non-fixed state.

The thickness of the covering tube 50 is preferably smaller than the thickness of the protective tube 60. When the thickness of the covering tube 50 is smaller than the thickness of the protective tube 60, it is possible to impart appropriate rigidity to the proximal side of the medical tubular body delivery device 1 to make the medical tubular body delivery device 1 have both pushability and flexibility. In addition, when the covering tube 50 is thinner than the protective tube 60, in addition to imparting appropriate rigidity, the members located inside the covering tube 50 are easily moved in the circumferential direction, so that pressing manipulability and manipulability for stent expansion are improved due to improvement of pushability. Furthermore, when the covering tube 50 has a smaller thickness, the overall dimension of the medical tubular body delivery device 1 can be reduced in diameter.

The thickness of the covering tube 50 is preferably not larger than 55%, more preferably not larger than 50%, and further preferably not larger than 45% of the thickness of the protective tube 60. When the upper limit of the ratio of the thickness of the covering tube 50 to the thickness of the outer tube 10 is set to be in the above range, the covering tube 50 is flexible. As a result, the flexibility necessary to make it easy for the members, which are disposed in the lumen of the covering tube 50, to move in the circumferential direction can be imparted to the covering tube 50. In addition, the thickness of the covering tube 50 is preferably not smaller than 5%, more preferably not smaller than 8%, and further preferably not smaller than 10% of the thickness of the outer tube 10. When the lower limit of the ratio of the thickness of the covering tube 50 to the thickness of the outer tube 10 is set to be in the above range, the covering tube 50 can have an excellent ability to hold the lumen thereof, that is, excellent so-called kink resistance.

The protective tube 60 has a distal-proximal direction and has a lumen extending in the distal-proximal direction, and the covering tube 50 is disposed in the lumen. That is, the covering tube 50 is disposed outward of the traction member housing tube 30 and the guide wire tube 80, and the protective tube 60 is disposed outward of the covering tube 50. Since the covering tube 50 is disposed in the lumen of the protective tube 60, the rigidity of the medical tubular body delivery device 1 can be increased, so that the traction member 20 is easily moved in the distal-proximal direction. As a result, it is easy to move the outer tube 10 in the distal-proximal direction, so that it is possible to stably perform indwelling of the medical tubular body 2.

Examples of the material of the protective tube 60 include synthetic resins including: polyolefin-based resins such as polyethylene and polypropylene; polyamide-based resins such as nylon; polyester-based resins such as PET; aromatic polyether ketone-based resins such as PEEK; polyether polyamide-based resins; polyurethane-based resins; polyimide-based resins; fluorine-based resins such as PTFE, PFA, and ETFE; polyvinyl chloride-based resins; and the like. Among them, the material of the protective tube 60 is preferably a fluorine-based resin, and more preferably PTFE. When the material of the protective tube 60 is a fluorine-based resin, the slidability between the protective tube 60 and the outer tube 10 is improved, so that it is easy to move the outer tube 10 in the distal-proximal direction.

Moreover, the protective tube 60 may have a single-layer structure, but preferably has a multi-layer structure. In the case where the protective tube 60 has a multi-layer structure, the protective tube 60 can have, for example, a structure in which a metal braid made of stainless steel, carbon steel, a nickel-titanium alloy, or the like is used as an intermediate layer of a resin tube that forms the protective tube 60. In addition, the intermediate layer of the resin tube that forms the protective tube 60 may be a coiled reinforcement layer. Among them, the protective tube 60 preferably has a metal braid made of stainless steel. When the protective tube 60 has a multi-layer structure, the rigidity of the protective tube 60 is increased, so that the rigidity of the entire medical tubular body delivery device 1 can also be improved. As a result, it is easy to move the outer tube 10 in the distal-proximal direction, so that it is possible to cause the medical tubular body 2 to stably indwell. Furthermore, in the case where the protective tube 60 has a multi-layer structure and a braided structure is used for the intermediate layer, the shape of the lumen of the protective tube 60 is easily maintained due to the braided structure even when the protective tube 60 is bent, so that kinking of the guide wire tube 80 and the traction member housing tube 30 can be prevented, and it can be easier to move a guide wire and the traction member 20 in the distal-proximal direction.

The thickness of the protective tube 60 is preferably larger than the thickness of the outer tube 10. When the thickness of the protective tube 60 is larger than the thickness of the outer tube 10, the rigidity of the protective tube 60 can be increased, so that it can be easier to move the outer tube 10 in the distal-proximal direction.

The thickness of the protective tube 60 is preferably not smaller than 1.1 times, more preferably not smaller than 1.2 times, and further preferably not smaller than 1.3 times the thickness of the outer tube 10. When the lower limit of the ratio of the thickness of the protective tube 60 to the thickness of the outer tube 10 is set to be in the above range, the rigidity of the protective tube 60 can be improved, so that it is easy to move the outer tube 10 in the distal-proximal direction. In addition, the thickness of the protective tube 60 is preferably not larger than 2.5 times, more preferably not larger than 2.25 times, and further preferably not larger than 2.0 times the thickness of the outer tube 10. When the upper limit of the ratio of the thickness of the protective tube 60 to the thickness of the outer tube 10 is set to be in the above range, it is possible to achieve both rigidity and flexibility of the protective tube 60.

The inner diameter of a distal end portion of the protective tube 60 is preferably larger than the outer diameter of the proximal end portion of the outer tube 10. In the case where the outer tube 10 has the reinforcement portion 11 on the proximal side, the connection tube 12 is provided between the outer tube 10 and the reinforcement portion 11, and the protective tube 60 is located outward of the reinforcement portion 11, the inner diameter of the distal end portion of the protective tube 60 is preferably larger than the outer diameter of the connection tube 12 of the outer tube 10. When the inner diameter of the distal end portion of the protective tube 60 is larger than the outer diameter of the proximal end portion of the outer tube 10, the proximal end portion of the outer tube 10 can be housed in the lumen of the protective tube 60 if the outer tube 10 is moved toward the proximal side. Therefore, when the outer tube 10 is moved in the distal-proximal direction, an increase in frictional resistance due to contact with the outside can be prevented, whereby the manipulation load can be reduced and more stable stent expansion can be performed.

The inner diameter of the distal end portion of the protective tube 60 is preferably not smaller than 102%, more preferably not smaller than 103%, and further preferably not smaller than 105% of the outer diameter of the proximal end portion of the outer tube 10. When the lower limit of the ratio of the inner diameter of the distal end portion of the protective tube 60 to the outer diameter of the proximal end portion of the outer tube 10 is set to be in the above range, it is easy to insert the outer tube 10 into the lumen of the protective tube 60. In addition, the inner diameter of the distal end portion of the protective tube 60 is preferably not larger than 200%, more preferably not larger than 170%, and further preferably not larger than 150% of the outer diameter of the proximal end portion of the outer tube 10. When the upper limit of the ratio of the inner diameter of the distal end portion of the protective tube 60 to the outer diameter of the proximal end portion of the outer tube 10 is set to be in the above range, the outer diameter of the protective tube 60 can be prevented from being excessively large. The inner diameter of the distal end portion of the protective tube 60 is preferably set to a value that is in a range where the outer tube 10 is movable and that is as close as possible to the outer diameter of the proximal end portion of the outer tube 10. When the inner diameter of the distal end portion of the protective tube 60 is set to a value that is as close as possible to the outer diameter of the proximal end portion of the outer tube 10, entry of a body fluid into the protective tube 60 can be minimized, so that the outer tube 10 is easily moved in the distal-proximal direction. In addition, the step between the distal end portion of the protective tube 60 and the outer tube 10 can be minimized, so that the distal end of the protective tube 60 can be prevented from being caught in the body.

In order to fix the traction member housing tube 30 and the guide wire tube 80 to each other on the distal side with respect to the distal end 50*a* of the covering tube 50 and on the proximal side with respect to the proximal end 10*b* of the outer tube 10, for example, as described above, the traction member housing tube 30 and the guide wire tube 80 are bonded, welded, fitted, or screwed, the traction member housing tube 30 and the guide wire tube 80 are inserted into a heat-shrinkable resin tube and the resin tube is heat-shrunk, or the traction member housing tube 30 and the guide wire tube 80 are inserted into a metal tube and the metal tube is crimped. Among them, as the method for fixing the traction member housing tube 30 and the guide wire tube 80 to each other, in the case where the traction member housing tube 30 and the guide wire tube 80 can be hot-melted, the traction member housing tube 30 and the guide wire tube 80 are preferably fixed by welding. When the traction member housing tube 30 and the guide wire tube 80 are fixed by welding, the rigidity of the portion where the traction member housing tube 30 and the guide wire tube 80 are fixed is increased, so that it is possible to improve the pushability of the medical tubular body delivery device 1. In the case where fixing by hot-melting is difficult, the traction member housing tube 30 and the guide wire tube 80 are preferably bonded by an adhesive. In addition, a plurality of fixing methods may be combined, such as combining bonding and welding. Specifically, for example, the traction member housing tube 30 and the guide wire tube 80 are fixed to each other by applying an adhesive to the traction member housing tube 30 and the guide wire tube 80, covering the traction member housing tube 30 and the guide wire tube 80 with heat-meltable tubular members, respectively, joining the traction member housing tube 30 and the guide wire tube 80 to the respective heat-meltable tubular members, and hot-melting the heat-meltable tubular member joined to the traction member housing tube 30 and the heat-meltable tubular member joined to the guide wire tube 80 to join the heat-meltable tubular members to each other. When the traction member housing tube 30 and the guide wire tube 80 are fixed by a combination of a plurality of fixing methods, the traction member housing tube 30 and the guide wire tube 80 can be firmly fixed to each other, so that the medical tubular body delivery device 1 can be prevented from being broken, and a procedure can be safely performed with the medical tubular body delivery device 1.

Examples of the adhesive for bonding the traction member housing tube 30 and the guide wire tube 80 include two-component adhesives, ultraviolet curable adhesives, and heat-curable adhesives, and the adhesive is preferably a two-component adhesive, and more preferably a two-component polyurethane adhesive. When a two-component adhesive is used as the adhesive for bonding the traction member housing tube 30 and the guide wire tube 80, the traction member housing tube 30 and the guide wire tube 80 can be firmly fixed to each other. In addition, as a method for fixing the traction member housing tube 30 and the guide wire tube 80 by melting a resin, a method of covering the traction member housing tube 30 and the guide wire tube 80 with a tube having an adhesive polyethylene on the inner surface thereof and then heat-shrinking the tube to fix the traction member housing tube 30 and the guide wire tube 80 by the adhesive polyethylene is also preferable. When the traction member housing tube 30 and the guide wire tube 80 are covered with the tube, and then the tube is heat-shrunk to fix the traction member housing tube 30 and the guide wire tube 80 to each other by the adhesive polyethylene, the traction member housing tube 30 and the guide wire tube 80 can be easily fixed to each other, and the fixing strength therebetween can be increased.

The length in the distal-proximal direction of a distal-side fixing portion 71 which fixes the traction member housing tube 30 and the guide wire tube 80 to each other on the distal side with respect to the distal end 50*a* of the covering tube 50 and on the proximal side with respect to the proximal end 10*b* of the outer tube 10 is preferably shorter than the length in the distal-proximal direction of the covering tube 50. When the length in the distal-proximal direction of the distal-side fixing portion 71 is shorter than the length in the distal-proximal direction of the covering tube 50, the traction member housing tube 30 and the guide wire tube 80 can be appropriately moved and deformed if the medical tubular body delivery device 1 is curved, so that the traction member 20 and the outer tube 10 are more easily moved in the distal-proximal direction.

The distal end 50*a* of the covering tube 50 and a proximal end 71*b* of the distal-side fixing portion 71 are preferably spaced apart from each other. That is, the distal end 50*a* of the covering tube 50 and the proximal end 71*b* of the distal-side fixing portion 71 are preferably not in contact with each other. When the distal end 50*a* of the covering tube 50 and the proximal end 71*b* of the distal-side fixing portion 71 are spaced apart from each other, the pushability of the medical tubular body delivery device 1 can be improved. Furthermore, when the distal end 50*a* of the covering tube 50 and the proximal end 71*b* of the distal-side fixing portion 71 are spaced apart from each other, the outer tube 10 can be easily moved in the distal-proximal direction even in a state where the medical tubular body delivery device 1 is curved. There is no problem if the distal end 50*a* of the covering tube 50 and the proximal end 71*b* of the distal-side fixing portion 71 are located completely without any gap therebetween, but when there is some gap with respect to the fixing portion, it is easier to move the members inside the covering tube 50 at the non-fixed portion in the circumferential direction. In particular, such a gap is effective in the case where the members inside the covering tube 50 have high rigidity. In addition, the length of the gap (portion where the covering tube 50 does not exist) is preferably set such that the members inside the covering tube 50 are not bent in the distal-proximal direction.

As shown in FIG. 5, in a cross-section orthogonal to the axial direction of the covering tube 50, the minor diameter of the lumen of the covering tube 50 is preferably smaller than the sum of the outer diameter of the traction member housing tube 30 and the outer diameter of the guide wire tube 80. The axial direction of the covering tube 50 refers to the longitudinal direction of the covering tube 50. When the minor diameter of the lumen of the covering tube 50 is smaller than the sum of the outer diameter of the traction member housing tube 30 and the outer diameter of the guide wire tube 80, a state where the traction member housing tube 30 and the guide wire tube 80, which are disposed in the lumen of the covering tube 50, are not fixed to each other can be obtained, and a state where the traction member housing tube 30 and the guide wire tube 80 can be prevented from moving in the distal-proximal direction and the radial direction and are movable only in the circumferential direction can be obtained in the lumen of the covering tube 50.

In the cross-section orthogonal to the axial direction of the covering tube 50, the minor diameter of the lumen of the covering tube 50 is preferably not larger than 0.95 times, more preferably not larger than 0.9 times, and further preferably not larger than 0.85 times the sum of the outer diameter of the traction member housing tube 30 and the outer diameter of the guide wire tube 80. When the upper limit of the ratio of the minor diameter of the lumen of the covering tube 50 to the sum of the outer diameter of the traction member housing tube 30 and the outer diameter of the guide wire tube 80 is set to be in the above range, it is possible to prevent the traction member housing tube 30 and the guide wire tube 80, which are disposed in the lumen of the covering tube 50, from excessively moving. In addition, the minor diameter of the lumen of the covering tube 50 is preferably not smaller than 0.3 times, more preferably not smaller than 0.35 times, and further preferably not smaller than 0.4 times the sum of the outer diameter of the traction member housing tube 30 and the outer diameter of the guide wire tube 80. When the lower limit of the ratio of the minor diameter of the lumen of the covering tube 50 to the sum of the outer diameter of the traction member housing tube 30 and the outer diameter of the guide wire tube 80 is set to be in the above range, it is easy to insert the traction member housing tube 30 and the guide wire tube 80 into the lumen of the covering tube 50, so that the efficiency in the production of the medical tubular body delivery device 1 can be improved.

As shown in FIG. 3, on the proximal side with respect to a proximal end 50*b* of the covering tube 50, the traction member housing tube 30 and the guide wire tube 80 are preferably fixed to each other. That is, preferably, the traction member housing tube 30 and the guide wire tube 80 are not fixed to each other at the portion where the covering tube 50 exists, the traction member housing tube 30 and the guide wire tube 80 are fixed to each other on the distal side with respect to the distal end 50*a* of the covering tube 50 and on both the proximal side with respect to the proximal end 10*b* of the outer tube 10 and the proximal side with respect to the proximal end 50*b* of the covering tube 50, the distal-side fixing portion 71 is provided on the distal side of the covering tube 50, and a proximal-side fixing portion 72 is provided on the proximal side of the covering tube 50.

When the traction member housing tube 30 and the guide wire tube 80 are fixed to each other on the proximal side with respect to the proximal end 50*b* of the covering tube 50, a pressing force applied to the hand side of the medical tubular body delivery device 1 is easily transmitted to the distal end, so that the medical tubular body delivery device 1 can have good pushability. In addition, it is possible for the traction member housing tube 30 and the guide wire tube 80 to move when the medical tubular body delivery device 1 is curved, so that the movement in the distal-proximal direction of the traction member 20 and the outer tube 10 can be less likely to be hindered.

The length in the distal-proximal direction of the distal-side fixing portion 71 may be shorter than the length in the distal-proximal direction of the proximal-side fixing portion 72, or may be equal to the length in the distal-proximal direction of the proximal-side fixing portion 72, but is preferably longer than the length in the distal-proximal direction of the proximal-side fixing portion 72. The distal-side fixing portion 71 is an important part that serves as a support during stent expansion. When the length in the distal-proximal direction of the distal-side fixing portion 71 is longer than the length in the distal-proximal direction of the proximal-side fixing portion 72, a sufficient length in the distal-proximal direction of the distal-side fixing portion 71 can be ensured, so that the outer tube 10 and the traction member 20 are easily moved in the distal-proximal direction. As a result, easy stent expansion can be enabled.

The proximal end 50*b* of the covering tube 50 and a distal end 72*a* of the proximal-side fixing portion 72 are preferably spaced apart and separated from each other. That is, the proximal end 50*b* of the covering tube 50 and the distal end 72*a* of the proximal-side fixing portion 72 are preferably not in contact with each other. When the proximal end 50*b* of the covering tube 50 and the distal end 72*a* of the proximal-side fixing portion 72 are spaced apart from each other, the outer tube 10 is easily moved in the distal-proximal direction even in a state where the medical tubular body delivery device 1 is curved, so that it is easy to cause the medical tubular body 2 to indwell, and further, the pushability of the medical tubular body delivery device 1 can be improved. There is no problem if the proximal end 50*b* of the covering tube 50 and the distal end 72*a* of the proximal-side fixing portion 72 are located completely without any gap therebetween, but when there is some gap with respect to the fixing portion, the members inside the covering tube 50 at the non-fixed portion are more easily moved in the circumferential direction. In particular, such a gap is effective in the case where the members inside the covering tube 50 have high rigidity. In addition, the length of the gap (portion where the covering tube 50 does not exist) is preferably set such that the members inside the covering tube 50 are not bent in the distal-proximal direction.

The thickness of the covering tube 50 is preferably smaller than the thickness of the protective tube 60, the thickness of the outer tube 10, and the thickness of the guide wire tube 80. When the thickness of the covering tube 50 is smaller than the thickness of the protective tube 60, the thickness of the outer tube 10, and the thickness of the guide wire tube 80, it is possible to prevent the outer diameter of the medical tubular body delivery device 1 from being excessively large, and to reduce the invasiveness of the medical tubular body delivery device 1. Furthermore, at the non-fixed portion, the movement in the circumferential direction of the members inside the covering tube 50 can be facilitated to improve the pushability and improve the manipulability for stent expansion.

The thickness of the guide wire tube 80 is preferably smaller than the thickness of the protective tube 60. When the thickness of the guide wire tube 80 is smaller than the thickness of the protective tube 60, the flexibility of the medical tubular body delivery device 1 can be increased. Therefore, it is easy to insert the medical tubular body delivery device 1 even into a curved in-vivo lumen.

The thickness of the guide wire tube 80 is preferably not larger than 90%, more preferably not larger than 80%, and further preferably not larger than 70% of the thickness of the protective tube 60. When the upper limit of the ratio of the thickness of the guide wire tube 80 to the thickness of the protective tube 60 is set to be in the above range, the flexibility of the guide wire tube 80 can be sufficiently increased. In addition, the thickness of the guide wire tube 80 is preferably not smaller than 30%, more preferably not smaller than 35%, and further preferably not smaller than 40% of the thickness of the protective tube 60. When the lower limit of the ratio of the thickness of the guide wire tube 80 to the thickness of the protective tube 60 is set to be in the above range, the rigidity of the guide wire tube 80 can be increased, so that the medical tubular body delivery device 1 can have good pushability.

Preferably, the guide wire tube 80 has the distal-side guide wire tube 81 and the proximal-side guide wire tube 82, the proximal end 81*b* of the distal-side guide wire tube 81 is located on the proximal side with respect to the distal end 71*a* of the distal-side fixing portion 71 at which the traction member housing tube 30 and the guide wire tube 80 are fixed to each other on the distal side with respect to the distal end 50*a* of the covering tube 50 and on the proximal side with respect to the proximal end 10*b* of the outer tube 10, and a distal end 82*a* of the proximal-side guide wire tube 82 is located on the distal side with respect to the proximal end 71*b* of the distal-side fixing portion 71. More preferably, the proximal end 71*b* of the distal-side fixing portion 71 and the distal end 82*a* of the proximal-side guide wire tube 82 are in contact with each other. When the proximal end 81*b* of the distal-side guide wire tube 81 is located on the proximal side with respect to the distal end 71*a* of the distal-side fixing portion 71, and the distal end 82*a* of the proximal-side guide wire tube 82 is located on the distal side with respect to the proximal end 71*b* of the distal-side fixing portion 71, the guide wire tube 80 having a long length in the distal-proximal direction is divided into the distal-side guide wire tube 81 and the proximal-side guide wire tube 82. Therefore, in the manufacture of the medical tubular body delivery device 1, the step of placing the guide wire tube 80 in the inner cavities of the outer tube 10 and the protective tube 60 is easily performed. In addition, for example, when the materials or shapes of the distal-side guide wire tube 81 and the proximal-side guide wire tube 82 are made different from each other, it is also possible to make the physical properties, etc., of the guide wire tube 80 different in the distal-proximal direction of the guide wire tube 80. Furthermore, the efficiency of load transmission in the distal-proximal direction of the medical tubular body delivery device 1 can be improved.

The distal end 30*a* of the traction member housing tube 30 is preferably located on the distal side with respect to the proximal end 81*b* of the distal-side guide wire tube 81. When the distal end 30*a* of the traction member housing tube 30 is located on the distal side with respect to the proximal end 81*b* of the distal-side guide wire tube 81, a load can be transmitted from the distal-side guide wire tube 81 directly to the traction member housing tube 30. As a result, manipulation for expanding the stent that is the medical tubular body 2 and manipulation for pressing the medical tubular body delivery device 1 can be easily performed.

The rigidity of the distal side of the guide wire tube 80 is preferably higher than the rigidity of the proximal side thereof. When the rigidity of the distal side of the guide wire tube 80 is higher than the rigidity of the proximal side thereof, the pushability of the medical tubular body delivery device 1 can be improved.

In order to make the rigidity of the distal side of the guide wire tube 80 higher than the rigidity of the proximal side thereof, for example, the guide wire tube 80 is configured to have the distal-side guide wire tube 81 and the proximal-side guide wire tube 82, and the rigidity of the distal-side guide wire tube 81 is made higher than the rigidity of the proximal-side guide wire tube 82. Specifically, preferably, the proximal-side guide wire tube 82 has a single-layer structure made of a synthetic resin, and the distal-side guide wire tube 81 has a multi-layer structure made of a synthetic resin and including a metal braid as an intermediate layer. Examples of the metal braid used for the distal-side guide wire tube 81 include metal braids made of stainless steel, carbon steel, a nickel-titanium alloy, and the like. Among them, the distal-side guide wire tube 81 preferably has a metal braid made of stainless steel. When the distal-side guide wire tube 81 has a multi-layer structure including a metal braid, it is easy to make the rigidity of the distal-side guide wire tube 81 higher than that of the proximal-side guide wire tube 82.

The medical tubular body delivery device 1 preferably has a wire 40 disposed outward of the traction member housing tube 30. The wire 40 is a linear member having a distal-proximal direction and is disposed outward of the traction member housing tube 30. When the medical tubular body delivery device 1 has the wire 40, the rigidity of the proximal side of the medical tubular body delivery device 1 can be increased, so that the pushability of the medical tubular body delivery device 1 can be improved.

Examples of the material of the wire 40 include metals such as stainless steel, iron, nickel, titanium, and alloys thereof, and synthetic resins including: polyolefin-based resins such as polyethylene and polypropylene; polyamide-based resins such as nylon; polyester-based resins such as PET; aromatic polyether ketone-based resins such as PEEK; polyether polyamide-based resins; polyurethane-based resins; polyimide-based resins; fluorine-based resins such as PTFE, PFA, and ETFE; polyvinyl chloride-based resins; and the like. Among them, the material of the wire 40 is preferably a metal, and more preferably stainless steel. When the material of the wire 40 is a metal, the rigidity of the proximal side of the medical tubular body delivery device 1 can be increased. In addition, when the material of the wire 40 is a metal, the outer diameter of the wire 40 can be prevented from being excessively large, and the outer diameter of the portion, of the medical tubular body delivery device 1, where the wire 40 exists can be prevented from being excessively large.

The outer diameter of the wire 40 is preferably larger than the outer diameter of the traction member 20. When the outer diameter of the wire 40 is larger than the outer diameter of the traction member 20, the rigidity of the proximal side of the medical tubular body delivery device 1 can be made higher than that of the distal side thereof. The outer diameter of the wire 40 may have a constant dimension in the distal-proximal direction, the outer diameter may change entirely or partially in a tapered shape from the proximal end of the wire 40 to the distal end of the wire 40, or the outer diameter may change stepwise. Moreover, the wire 40 may be a wire having a semicircular or square cross-section perpendicular to the distal-proximal direction. In addition, the wire 40 may be a wire having a flat plate shape, a coil wire shape, or a hollow shape. Furthermore, the wire 40 may have a structure obtained by combining the shapes described here.

The outer diameter of the wire 40 is preferably not smaller than 1.1 times, more preferably not smaller than 1.2 times, and further preferably not smaller than 1.3 times the outer diameter of the traction member 20. When the lower limit of the ratio of the outer diameter of the wire 40 to the outer diameter of the traction member 20 is set to be in the above range, sufficient rigidity can be imparted to the proximal side of the medical tubular body delivery device 1. In addition, the outer diameter of the wire 40 is preferably not larger than 5 times, more preferably not larger than 4 times, and further preferably not larger than 3 times the outer diameter of the traction member 20. When the upper limit of the ratio of the outer diameter of the wire 40 to the outer diameter of the traction member 20 is set to be in the above range, it is possible to prevent the outer diameter of the wire 40 from being excessively increased, while ensuring appropriate rigidity that serves as a support during stent expansion.

The outer diameter of the guide wire tube 80 is preferably larger than both the outer diameter of the traction member housing tube 30 and the outer diameter of the wire 40. When the outer diameter of the guide wire tube 80 is larger than both the outer diameter of the traction member housing tube 30 and the outer diameter of the wire 40, the rigidity of the medical tubular body delivery device 1 can be increased. Therefore, it is easy to insert the medical tubular body delivery device 1 to a target location along the guide wire placed in the body.

The outer diameter of the guide wire tube 80 is preferably not smaller than 1.1 times, more preferably not smaller than 1.2 times, and further preferably not smaller than 1.3 times the larger outer diameter out of the outer diameters of the traction member housing tube 30 and the wire 40. When the lower limit of the ratio of the outer diameter of the guide wire tube 80 to the outer diameter of the traction member housing tube 30 or the wire 40 is set to be in the above range, the rigidity of the medical tubular body delivery device 1 can be sufficiently increased, so that the pushability of the medical tubular body delivery device 1 can be improved. In addition, the outer diameter of the guide wire tube 80 is preferably not larger than 3.5 times, more preferably not larger than 3.3 times, and further preferably not larger than 3.0 times the larger outer diameter out of the outer diameters of the traction member housing tube 30 and the wire 40. When the upper limit of the ratio of the outer diameter of the guide wire tube 80 to the outer diameter of the traction member housing tube 30 or the wire 40 is set to be in the above range, a situation in which the outer diameter of the guide wire tube 80 becomes excessively large and thus the outer diameter of the medical tubular body delivery device 1 also becomes excessively large can be prevented.

Preferably, the wire 40 disposed outward of the traction member housing tube 30 is provided, and the traction member housing tube 30, the guide wire tube 80, and the wire 40 are fixed to each other on the distal side with respect to the distal end 50*a* of the covering tube 50. That is, the traction member housing tube 30, the guide wire tube 80, and the wire 40 are preferably fixed to each other at the distal-side fixing portion 71, and the distal end 40*a* of the wire 40 is more preferably located on the distal side with respect to a proximal end 81*b* of a distal-side guide wire tube 81 in the distal-side fixing portion 71. When the wire 40 is disposed outward of the traction member housing tube 30, and the traction member housing tube 30, the guide wire tube 80, and the wire 40 are fixed to each other on the distal side with respect to the distal end 50*a* of the covering tube 50, the rigidity of the medical tubular body delivery device 1 can be increased, so that the pushability of the medical tubular body delivery device 1 and a force that presses the medical tubular body 2 from the outer tube 10 can be improved. Therefore, it is possible to stably and easily perform indwelling of the medical tubular body 2. In addition, axial compression resistance can be added to the distal-side guide wire tube 81 on which the compressive load during stent expansion acts directly.

In the cross-section orthogonal to the axial direction of the covering tube 50, the minor diameter of the lumen of the covering tube 50 is preferably smaller than the sum of the outer diameters of the two members having larger outer diameters out of the traction member housing tube 30, the guide wire tube 80, and the wire 40. When the minor diameter of the lumen of the covering tube 50 is smaller than the sum of the outer diameters of the two members having larger outer diameters out of the traction member housing tube 30, the guide wire tube 80, and the wire 40, a state where the traction member housing tube 30, the guide wire tube 80, and the wire 40, which are disposed in the lumen of the covering tube 50, are not fixed to each other can be obtained, and a state where the traction member housing tube 30, the guide wire tube 80, and the wire 40 are prevented from moving in the distal-proximal direction and the radial direction and are movable only in the circumferential direction can be obtained in the lumen of the covering tube 50. As a result, the outer tube 10 is easily moved in the distal-proximal direction, so that the medical tubular body 2 can be easily caused to indwell.

In the cross-section orthogonal to the axial direction of the covering tube 50, the minor diameter of the lumen of the covering tube 50 is preferably not larger than 0.95 times, more preferably not larger than 0.9 times, and further preferably not larger than 0.85 times the sum of the outer diameters of the two members having larger outer diameters out of the traction member housing tube 30, the guide wire tube 80, and the wire 40. When the upper limit of the ratio of the minor diameter of the lumen of the covering tube 50 to the sum of the outer diameters of the two members having larger outer diameters out of the traction member housing tube 30, the guide wire tube 80, and the wire 40 is set to be in the above range, the traction member housing tube 30, the guide wire tube 80, and the wire 40 are easily maintained in a non-fixed state in the lumen of the covering tube 50. As a result, the traction member housing tube 30, the guide wire tube 80, and the wire 40 are easily moved in the circumferential direction, leading to improvement in pushability and improvement in manipulation for stent expansion. In addition, the minor diameter of the lumen of the covering tube 50 is preferably not smaller than 0.3 times, more preferably not smaller than 0.35 times, and further preferably not smaller than 0.4 times the sum of the outer diameters of the two members having larger outer diameters out of the traction member housing tube 30, the guide wire tube 80, and the wire 40. When the lower limit of the ratio of the minor diameter of the lumen of the covering tube 50 to the sum of the outer diameters of the two members having larger outer diameters out of the traction member housing tube 30, the guide wire tube 80, and the wire 40 is set to be in the above range, it is easy to insert the traction member housing tube 30, the guide wire tube 80, and the wire 40 into the lumen of the covering tube 50 in the manufacture of the medical tubular body delivery device 1. As a result, it is possible to improve the production efficiency of the medical tubular body delivery device 1.

A distal end 40*a* of the wire 40 is preferably located on the proximal side with respect to a distal end 71*a* of the distal-side fixing portion 71 and on the distal side with respect to the proximal end 71*b* of the distal-side fixing portion 71 at which the traction member housing tube 30 and the guide wire tube 80 are fixed to each other on the distal side with respect to the distal end 50*a* of the covering tube 50 and on the proximal side with respect to the proximal end 10*b* of the outer tube 10. That is, the distal end 40*a* of the wire 40 is preferably located inward of the distal-side fixing portion 71. When the distal end 40*a* of the wire 40 is located on the proximal side with respect to the distal end 71*a* of the distal-side fixing portion 71 and on the distal side with respect to the proximal end 71*b* of the distal-side fixing portion 71, the pushability can be improved to reinforce the axial compression resistance during stent expansion, facilitating the movement in the distal-proximal direction of the outer tube 10 and the reinforcement portion 11. In addition, even when a state where the medical tubular body delivery device 1 is greatly curved, such as when the medical tubular body delivery device 1 is placed in a greatly curved in-vivo lumen, a situation in which the end portion of the wire 40 comes into contact with another member such as the protective tube 60 to damage the other member can be prevented.

Although not shown, a proximal end 40*b* of the wire 40 is preferably also located on the distal side with respect to the proximal end 50*b* of the covering tube 50. In addition, in the case where the proximal-side fixing portion 72 is not provided, the proximal end 40*b* of the wire 40 is preferably located on the distal side with respect to the proximal end 50*b* of the covering tube 50, that is, in the covering tube 50. In the case where the proximal-side fixing portion 72 is provided, the proximal end 40*b* of the wire 40 may be located in the proximal-side fixing portion 72. When the proximal end 40*b* of the wire 40 is located on the distal side with respect to the proximal end 50*b* of the covering tube 50, the proximal end 40*b* of the wire 40 is located inward of the covering tube 50, and the proximal end 40*b* of the wire 40 is less likely to come into contact with another member to damage the other member even if the proximal-side fixing portion 72 is not provided. Therefore, the steps for manufacturing the medical tubular body delivery device 1 can be reduced, so that the production efficiency can be improved. In addition, since the proximal end 40*b* of the wire 40 is prevented from coming into contact with another member, the durability of the medical tubular body delivery device 1 can be improved.

A distal end 30*a* of the traction member housing tube 30 is preferably located on the distal side with respect to the distal end 71*a* of the distal-side fixing portion 71 at which the traction member housing tube 30 and the wire 40 are fixed to each other on the distal side with respect to the distal end 50*a* of the covering tube 50 and on the proximal side with respect to the proximal end 10*b* of the outer tube 10. When the distal end 30*a* of the traction member housing tube 30 is located on the distal side with respect to the distal end 71*a* of the distal-side fixing portion 71, it is easy to insert the traction member 20 into the lumen of the traction member housing tube 30 in the manufacture of the medical tubular body delivery device 1, so that the production efficiency can be improved.

As shown in FIG. 1 and FIG. 2, the medical tubular body delivery device 1 preferably has a tip 3 which is more flexible than the outer tube 10, at a distal end portion thereof.

In addition, the outer diameter of the distal end of the tip 3 may be equal to or larger than the outer diameter of the distal end of the outer tube 10, but is more preferably smaller than the outer diameter of the distal end of the outer tube 10. When the medical tubular body delivery device 1 has the tip 3, which is more flexible than the outer tube 10, at the distal end portion thereof, the distal end of the medical tubular body delivery device 1 can be prevented from damaging the inside of the body, and the followability to bending, the followability to the preceding guide wire, and the reachability to the periphery can be improved, when delivering the medical tubular body delivery device 1 into the body, so that the manipulability during delivery is improved. In addition, since the proximal end of the tip 3 extends toward the proximal side beyond the distal end of the outer tube 10, the outer tube 10 easily follows the bent tip 3, making such a structure more preferable.

Examples of the material of the tip 3 include synthetic resins including: polyolefin-based resins such as polyethylene and polypropylene; polyamide-based resins such as nylon; polyester-based resins such as PET; aromatic polyether ketone-based resins such as PEEK; polyether polyamide-based resins; polyurethane-based resins; polyimide-based resins; fluorine-based resins such as PTFE, PFA, and ETFE; polyvinyl chloride-based resins; and the like. Among them, the material of the tip 3 is preferably a polyamide-based resin, and more preferably a polyamide elastomer. When the material of the tip 3 is a polyamide-based resin, the medical tubular body delivery device 1 can achieve both followability of the tip 3 to the guide wire and safety of the distal end.

As shown in FIG. 1, the medical tubular body delivery device 1 may have a controller 4 on the proximal side thereof. Preferably, a proximal end portion of the traction member 20 is fixed to the controller 4, and the traction member 20 is movable in the distal-proximal direction by manipulating the controller 4. When the medical tubular body delivery device 1 has the controller 4 on the proximal side thereof, the traction member 20 is easily moved in the distal-proximal direction. As a result, the outer tube 10 is easily moved in the distal-proximal direction, and it is easy to cause the medical tubular body 2 to indwell at a lesion site.

As shown in FIG. 2, the medical tubular body delivery device 1 preferably has a stopper 5 for limiting the position of the medical tubular body 2 in the lumen of the outer tube 10 and pressing the medical tubular body 2 toward the distal side. When the medical tubular body delivery device 1 has the stopper 5, it is easy to release the medical tubular body 2 from the outer tube 10 and cause the medical tubular body 2 to indwell at the lesion site.

The shape of the stopper 5 can be, for example, a ring shape, and the outer diameter thereof is preferably equal to or smaller than the outer diameter of the medical tubular body 2 in a state where the medical tubular body 2 is housed in the lumen of the outer tube 10, and smaller than the inner diameter of the outer tube 10. When the shape of the stopper 5 is a ring shape whose outer diameter is equal to or smaller than the outer diameter of the medical tubular body 2 in a state where the medical tubular body 2 is housed in the lumen of the outer tube 10, and smaller than the inner diameter of the outer tube 10, the stopper 5 is less likely to hinder the movement in the distal-proximal direction of the outer tube 10 and can sufficiently press the medical tubular body 2.

The material of the stopper 5 is preferably an elastic resin material, and examples of the material of the stopper 5 include polyolefin-based resins such as polyethylene, fluorine-based resins such as PTFE and PFA, polyamide-based resins, polyurethane-based resins, polyester-based resins, and silicone-based resins. Among them, the material of the stopper 5 is preferably a polyamide-based resin. When the material of the stopper 5 is a polyamide-based resin, the rigidity of the stopper 5 can be increased, the rear end of the medical tubular body 2 such as a stent can be supported, and the stent can be efficiently expanded. In addition, the polyamide-based resin is easily molded and thus also has an effect of facilitating the manufacture of the stopper 5.

The medical tubular body delivery device 1 may have an X-ray opaque marker 6. When the medical tubular body delivery device 1 has the X-ray opaque marker 6, the position at which the X-ray opaque marker 6 is provided can be confirmed under X-ray fluoroscopy. As shown in FIG. 2, the X-ray opaque marker 6 is preferably provided, for example, at the location where the tip 3 is disposed or at the location where the stopper 5 is disposed. When the X-ray opaque marker 6 is provided at the location where the tip 3 is disposed, the distal end portion of the medical tubular body delivery device 1 can be confirmed under X-ray fluoroscopy. In addition, when the X-ray opaque marker 6 is provided at the location where the stopper 5 is disposed, the position or the pressed-out state of the medical tubular body 2 can be confirmed under X-ray fluoroscopy. The number of X-ray opaque markers 6 may be one or a plural number.

Examples of the shape of the X-ray opaque marker 6 include a cylindrical shape, a polygonal tubular shape, a shape having a C-shaped cross section and obtained by forming a slit in a cylinder, and a coil shape obtained by winding a wire. Among them, the shape of the X-ray opaque marker 6 is preferably a cylindrical shape. When the shape of the X-ray opaque marker 6 is a cylindrical shape, uniform visibility in the circumferential direction can be imparted to the X-ray opaque marker 6, so that the visibility under X-ray fluoroscopy can be improved.

As the material of the X-ray opaque marker 6, for example, an X-ray opaque substance such as lead, barium, iodine, tungsten, gold, platinum, iridium, stainless steel, tantalum, titanium, a cobalt-chromium alloy, or the like can be used. Among them, the X-ray opaque substance is preferably platinum. When the X-ray opaque substance for forming the X-ray opaque marker 6 is platinum, the X-ray imaging property can be enhanced.

The method for manufacturing the medical tubular body delivery device 1 of the present invention includes: a first step of inserting the traction member housing tube 30 into the lumen of the covering tube 50; a second step of inserting the guide wire tube 80 into the lumen of the covering tube 50; and a third step of fixing the traction member housing tube 30 and the guide wire tube 80 to each other on the distal side with respect to the distal end 50*a* of the covering tube 50. When the medical tubular body delivery device 1 is manufactured by such a method, the medical tubular body delivery device 1 can be easily manufactured, and it is possible to improve the production efficiency.

In the first step, the traction member housing tube 30 is inserted into the lumen of the covering tube 50. In the first step, the distal end 30*a* of the traction member housing tube 30 may be inserted into the lumen of the covering tube 50 through the proximal end 50*b* of the covering tube 50, or the proximal end of the traction member housing tube 30 may be inserted into the lumen of the covering tube 50 through the distal end 50*a* of the covering tube 50.

In the second step, the guide wire tube 80 is inserted into the lumen of the covering tube 50. In the second step, the distal end of the guide wire tube 80 may be inserted into the lumen of the covering tube 50 through the proximal end 50*b* of the covering tube 50, or the proximal end of the guide wire tube 80 may be inserted into the lumen of the covering tube 50 through the distal end 50*a* of the covering tube 50.

In the case of inserting the proximal end of the traction member housing tube 30 into the lumen of the covering tube 50 through the distal end 50*a* of the covering tube 50, the proximal end of the guide wire tube 80 is preferably inserted through the distal end 50*a* of the covering tube 50. That is, preferably, the proximal end of the traction member housing tube 30 is inserted into the lumen of the covering tube 50 through the distal end 50*a* of the covering tube 50 in the first step, and the proximal end of the guide wire tube 80 is inserted into the lumen of the covering tube 50 through the distal end 50*a* of the covering tube 50 in the second step. When the proximal end of the traction member housing tube 30 is inserted into the lumen of the covering tube 50 through the distal end 50*a* of the covering tube 50 in the first step, and the proximal end of the guide wire tube 80 is inserted into the lumen of the covering tube 50 through the distal end 50*a* of the covering tube 50 in the second step, the covering tube 50 is prevented from being broken when inserting the traction member housing tube 30 or the guide wire tube 80 into the lumen of the covering tube 50, and it is easy to insert the traction member housing tube 30 and the wire 40 into the covering tube 50. Therefore, the production efficiency of the medical tubular body delivery device 1 can be improved.

The second step may be performed before the first step, or may be performed after the first step, but the first step and the second step are preferably performed simultaneously. That is, the traction member housing tube 30 and the guide wire tube 80 are preferably placed together in the lumen of the covering tube 50. When the first step and the second step are performed simultaneously, it is easy to perform the step of inserting the traction member housing tube 30 and the guide wire tube 80 into the lumen of the covering tube 50. As a result, the productivity of the medical tubular body delivery device 1 can be increased.

In the case where the medical tubular body delivery device 1 has the wire 40, a step of inserting the wire 40 into the lumen of the covering tube 50 may be included. This step may be performed before the first step, simultaneously with the first step, or after the first step, or may be performed before the second step, simultaneously with the second step, or after the second step. Among them, the step of inserting the wire 40 into the lumen of the covering tube 50 is preferably performed after the first step and the second step. When the step of inserting the wire 40 into the lumen of the covering tube 50 is performed after the first step and the second step, it is easy to insert the wire 40 into the lumen of the covering tube 50, and a situation in which the end portion of the wire 40 becomes caught at the covering tube 50 to break the covering tube 50 is prevented, so that it is possible to improve the production efficiency of the medical tubular body delivery device 1. When the member having a smallest outer diameter out of the traction member housing tube 30, the guide wire tube 80, and the wire 40 is inserted into the lumen of the covering tube 50 last among these members, the medical tubular body delivery device 1 can be efficiently assembled. This is because the two members having larger outer diameters out of the traction member housing tube 30, the guide wire tube 80, and the wire 40 are in a state where the movement in the radial direction thereof is hindered by the covering tube 50, and thus it is easy to insert the member having a smallest outer diameter into a gap formed by these two members.

In the case where the medical tubular body delivery device 1 has the wire 40, the proximal end of the traction member housing tube 30 is inserted into the lumen of the covering tube 50 through the distal end 50*a* of the covering tube 50 in the first step, and the proximal end of the guide wire tube 80 is inserted into the lumen of the covering tube 50 through the distal end 50*a* of the covering tube 50 in the second step, the proximal end 40*b* of the wire 40 is preferably inserted into the lumen of the covering tube 50 through the distal end 50*a* of the covering tube 50. When the proximal end 40*b* of the wire 40 is inserted into the lumen of the covering tube 50 through the distal end 50*a* of the covering tube 50, it is easy to insert the wire 40 into the lumen of the covering tube 50, and a situation in which the end portion of the wire 40 becomes caught at the covering tube 50 to break the covering tube 50 can be prevented.

In the third step, the traction member housing tube 30 and the guide wire tube 80 are fixed to each other on the distal side with respect to the distal end 50*a* of the covering tube 50. As a method for fixing the traction member housing tube 30 and the guide wire tube 80 to each other, for example, the traction member housing tube 30 and the guide wire tube 80 are bonded, welded, or fitted, the traction member housing tube 30 and the guide wire tube 80 are inserted into a heat-shrinkable resin tube and the resin tube is heat-shrunk, or the traction member housing tube 30 and the guide wire tube 80 are inserted into a metal tube and the metal tube is crimped. Among them, in the case where it is possible to join the traction member housing tube 30 and the guide wire tube 80 to each other by hot-melting, the traction member housing tube 30 and the guide wire tube 80 are preferably fixed by welding. When the traction member housing tube 30 and the guide wire tube 80 are fixed to each other by welding in the third step, the traction member housing tube 30 and the guide wire tube 80 can be easily fixed firmly. In the case where it is difficult to join the traction member housing tube 30 and the guide wire tube 80 by hot-melting, the traction member housing tube 30 and the guide wire tube 80 are preferably bonded by an adhesive. In addition, bonding and welding may be combined. Specifically, for example, the traction member housing tube 30 and the guide wire tube 80 are fixed to each other by applying an adhesive to the traction member housing tube 30 and the guide wire tube 80, covering the traction member housing tube 30 and the guide wire tube 80 with heat-meltable tubular members, respectively, joining the traction member housing tube 30 and the guide wire tube 80 to the respective heat-meltable tubular members, and hot-melting the heat-meltable tubular member joined to the traction member housing tube 30 and the heat-meltable tubular member joined to the guide wire tube 80 to join the heat-meltable tubular members to each other. When the traction member housing tube 30 and the guide wire tube 80 are fixed to each other by a combination of bonding and welding in the third step, it is possible to firmly fix the traction member housing tube 30 and the guide wire tube 80, and also easily fix the traction member housing tube 30 and the guide wire tube 80.

The third step may be performed before the first step and the second step, but is preferably performed after the first step and the second step. When the third step is performed after the first step and the second step, it is easy to fix the traction member housing tube 30 and the guide wire tube 80. Therefore, the production efficiency of the medical tubular body delivery device 1 can be improved.

In the case where the medical tubular body delivery device 1 has the wire 40, the traction member housing tube 30, the guide wire tube 80, and the wire 40 are preferably fixed to each other on the distal side with respect to the distal end 50*a* of the covering tube 50 in the third step. When the traction member housing tube 30, the guide wire tube 80, and the wire 40 are fixed to each other on the distal side with respect to the distal end 50*a* of the covering tube 50 in the third step, the traction member housing tube 30, the guide wire tube 80, and the wire 40 can be easily and firmly fixed, so that it is possible to prevent the medical tubular body delivery device 1 from being broken. In addition, the distal end 30*a* of the traction member housing tube 30 is preferably placed and fixed on the distal side with respect to the proximal end 81*b* of the distal-side guide wire tube 81. When the distal end 30*a* of the traction member housing tube 30 is placed and fixed on the distal side with respect to the proximal end 81*b* of the distal-side guide wire tube 81, a load can be transmitted from the distal-side guide wire tube 81 directly to the traction member housing tube 30. Therefore, manipulation for stent expansion or pressing can be easily performed.

A step of fixing the traction member housing tube 30 and the guide wire tube 80 to each other on the proximal side with respect to the proximal end 50*b* of the covering tube 50 may be included. This step is preferably performed after the first step and the second step. Alternatively, this step may be performed before the third step or after the third step. When the step of fixing the traction member housing tube 30 and the wire 40 to each other on the proximal side with respect to the proximal end 50*b* of the covering tube 50 is included, the pushability of the medical tubular body delivery device 1 can be improved, so that it is easy to cause the medical tubular body 2 to indwell at a target site.

As described above, the medical tubular body delivery device of the present invention is a device for delivering a medical tubular body into a body, the device including: an outer tube having a lumen in which the medical tubular body is disposed; a traction member connected to the outer tube; a traction member housing tube having a lumen into which the traction member is inserted; a guide wire tube having a lumen into which a guide wire is to be inserted; a covering tube having a lumen in which the traction member housing tube and the guide wire tube are disposed; and a protective tube having a lumen in which the covering tube is disposed, wherein the traction member housing tube and the guide wire tube are fixed to each other on a distal side with respect to a distal end of the covering tube and on a proximal side with respect to a proximal end of the outer tube, and the traction member housing tube and the guide wire tube are not fixed to each other at a portion where the covering tube exists. Owing to such a configuration, large frictional resistance is less likely to be generated between the outer tube and another member when moving the outer tube in the distal-proximal direction, so that the manipulation resistance of the medical tubular body delivery device can be reduced. In addition, since the protective tube is included, the rigidity of the medical tubular body delivery device can be increased, it can be easy to move the outer tube in the distal-proximal direction, and indwelling of the medical tubular body can be stably performed.

The present application claims the benefit of priority based on Japanese patent application number 2019-057272 filed on Mar. 25, 2019. The entire content of the specification of Japanese patent application number 2019-057272 filed on Mar. 25, 2019 is incorporated herein by reference.

DESCRIPTION OF REFERENCE SIGNS

1 medical tubular body delivery device
2 medical tubular body
3 tip
4 controller
5 stopper
6 X-ray opaque marker
10 outer tube
10*b* proximal end of the outer tube
11 reinforcement portion
12 connection tube
20 traction member
30 traction member housing tube
30*a* distal end of the traction member housing tube
40 wire
40*a* distal end of the wire
40*b* proximal end of the wire
50 covering tube
50*a* distal end of the covering tube
50*b* proximal end of the covering tube
60 protective tube
71 distal-side fixing portion
71*a* distal end of the distal-side fixing portion
71*b* proximal end of the distal-side fixing portion
72 proximal-side fixing portion
72*a* distal end of the proximal-side fixing portion
80 guide wire tube
81 distal-side guide wire tube
81*b* proximal end of the distal-side guide wire tube
82 proximal-side guide wire tube
82*a* distal end of the proximal-side guide wire tube

The invention claimed is:

1. A medical tubular body delivery device for delivering a medical tubular body into a body, the medical tubular body delivery device comprising:

an outer tube having a lumen, in which the medical tubular body is disposed, the outer tube disposed at a distal side of the medical tubular body delivery device such that the medical tubular body can be delivered from a distal end of the outer tube into the body;

a traction member connected to the outer tube;

a traction member housing tube having a lumen into which the traction member is inserted;

a guide wire tube having a lumen, into which a guide wire is to be inserted;

a covering tube having a lumen in which the traction member housing tube and the guide wire tube are disposed; and a protective tube having a lumen in which the covering tube is disposed, wherein the traction member housing tube and the guide wire tube are fixed to each other by at least one of bonding, welding, fitting, screwing, or crimping on a distal side with respect to a distal end of the covering tube and on a proximal side with respect to a proximal end of the outer tube, so that the traction member housing tube cannot move with respect to the guide wire tube in the axial direction of the covering tube, and the traction member housing tube and the guide wire tube are not fixed to each other at a portion where the covering tube exists, so that the traction member housing tube and the guide wire tube can move with respect to the covering tube in an axial direction of the covering tube.

2. The medical tubular body delivery device according to claim 1, wherein, in a cross-section orthogonal to the axial direction of the covering tube, a minor diameter of the lumen of the covering tube is smaller than a sum of an outer diameter of the traction member housing tube and an outer diameter of the guide wire tube.

3. The medical tubular body delivery device according to claim 1, wherein the traction member housing tube and the guide wire tube are fixed to each other on the proximal side with respect to a proximal end of the covering tube.

4. The medical tubular body delivery device according to claim 1, wherein a thickness of the covering tube is smaller than a thickness of the protective tube, a thickness of the outer tube, and a thickness of the guide wire tube.

5. The medical tubular body delivery device according to claim 1, further comprising a wire disposed outside of the traction member housing tube, wherein the traction member housing tube, the guide wire tube, and the wire are fixed to each other on the distal side with respect to the distal end of the covering tube.

6. The medical tubular body delivery device according to claim 5, wherein, in the cross-section orthogonal to the axial direction of the covering tube, the minor diameter of the lumen of the covering tube is smaller than a sum of outer diameters of two members having a largest outer diameter and a second largest outer diameter out of the traction member housing tube, the guide wire tube, and the wire.

7. The medical tubular body delivery device according to claim 5, wherein the traction member housing tube and the guide wire tube are fixed to each other at a distal-side fixing portion located between the distal end of the covering tube and the proximal end of the outer tube, and a distal end of the wire is located between a distal end of the distal-side fixing portion and a proximal end of the distal-side fixing portion.

8. The medical tubular body delivery device according to any claim 5, wherein a proximal end of the wire is located on the distal side with respect to the proximal end of the covering tube.

9. A method for manufacturing the medical tubular body delivery device according to claim 1, the method comprising the steps of providing the outer tube, the traction member, the traction member housing tube, the guide wire tube, the covering tube, and the protective tube;

inserting the traction member housing tube into the lumen of the covering tube;

inserting the guide wire tube into the lumen of the covering tube;

fixing the traction member housing tube and the guide wire tube to each other;

inserting the traction member into the lumen of the traction member housing tube;

connecting the traction member to the outer tube;

and inserting the covering tube into the lumen of the protective tube, wherein the traction member housing tube and the guide wire tube are fixed to each other by at least one of bonding, welding, fitting, screwing, or crimping on the distal side with respect to the distal end of the covering tube and on the proximal side with respect to the proximal end of the outer tube, so that the traction member housing tube cannot move with respect to the guide wire tube in the axial direction of the covering tube and the traction member housing tube and the guide wire tube are not fixed to each other at a portion where the covering tube exists, so that the traction member housing tube and the guide wire tube can move with respect to the covering tube in an axial direction of the covering tube.

10. The method for manufacturing the medical tubular body delivery device according to claim 9, wherein in the step of inserting the traction member housing tube into the lumen of the covering tube, a proximal end of the traction member housing tube is inserted into the lumen of the covering tube through the distal end of the covering tube, and in the step of inserting the guide wire tube into the lumen of the covering tube, the proximal end of the guide wire tube is inserted into the lumen of the covering tube through the distal end of the covering tube.

* * * * *